US006742892B2

(12) United States Patent
Liberman

(10) Patent No.: US 6,742,892 B2
(45) Date of Patent: Jun. 1, 2004

(54) DEVICE AND METHOD FOR EXERCISING EYES

(75) Inventor: Jacob Liberman, Kula, HI (US)

(73) Assignee: Exercise Your Eyes, LLC, Santa Margarita, CA (US)

(*) Notice: Subject to any disclaimer, the term of this patent is extended or adjusted under 35 U.S.C. 154(b) by 0 days.

(21) Appl. No.: 10/123,594

(22) Filed: Apr. 16, 2002

(65) Prior Publication Data

US 2003/0193646 A1 Oct. 16, 2003

(51) Int. Cl.[7] ........ A61B 3/00
(52) U.S. Cl. ........ 351/203
(58) Field of Search ........ 351/200, 203, 351/209, 222, 223, 213, 221, 232, 233, 237, 246

(56) References Cited

U.S. PATENT DOCUMENTS

| | | | | |
|---|---|---|---|---|
| 2,110,344 A | | 3/1938 | Taylor et al. | |
| 2,735,423 A | * | 2/1956 | Powell | 351/203 |
| 2,840,073 A | | 6/1958 | Zeltzer et al. | |
| 4,756,305 A | | 7/1988 | Mateik et al. | |
| 4,824,237 A | | 4/1989 | Ratner et al. | |
| 4,940,323 A | | 7/1990 | Downing | |
| 5,051,931 A | | 9/1991 | Cheu et al. | |
| 5,088,810 A | | 2/1992 | Galanter et al. | |
| 5,092,669 A | | 3/1992 | Anderson | |
| 5,305,027 A | | 4/1994 | Patterson | |
| 5,343,261 A | * | 8/1994 | Wilson | 351/203 |
| 5,417,573 A | * | 5/1995 | Cassiere, II et al. | 434/21 |
| 5,455,643 A | | 10/1995 | Ki-Ho | |
| 5,515,069 A | * | 5/1996 | Dillon, III | 345/6 |
| 5,520,543 A | | 5/1996 | Mitui | |
| 5,781,274 A | | 7/1998 | Moreno | |
| 5,812,239 A | | 9/1998 | Eger | |
| 6,139,149 A | | 10/2000 | Shafer et al. | |

OTHER PUBLICATIONS

Bennett, Arthur, et al.; Clinical Visual Optics, 1989, 2nd Edition, pp. 332–336.*

Sears, Francis Weston, et al.; Chapter 45 Color, College Physics, 1952, pp. 813–827, Second Edition, Addison–Wesley Press, Cambridge, MA.

Bennett, Arthur, et al.; Clinical Visual Optics, 1989, Second Edition, pp. 332–336.

Freeman, M.H.; Optics, 1990, Tenth Edition, pp. 494–496.

Wayne Engineering, Wayne Enginerering Catalog, Vis–Flex Visual Flexibility Trainer, circa 1986.

Manual, "Preliminary Instructions on the Use of the Liberman Vis–Flex", circa 1986.

Bennet, et al. Clinical Visual Optics, 2nd Edition, 1989, pp. 332–336.

* cited by examiner

*Primary Examiner*—Dennis W. Ruhl
*Assistant Examiner*—John R. Sanders
(74) *Attorney, Agent, or Firm*—Lerner, David, Littenberg, Krumholz & Mentlik, LLP

(57) ABSTRACT

A device and method is provided for eye exercise. The eye exercise device includes a housing with colored light sources of at least two different colors in a substantially linear alignment, including a first color which causes the eye to increase its focusing power to gain a sharp image of the first color, and a second color which causes the eye to decrease the focusing power to gain a sharp image of the second color. A controller may control the display of the light sources to an observer. A method of exercising eyes is provided that includes exposing an observer to red and blue light sources, and activating one or more of the light sources to display the light sources to the observer one-at-a-time.

33 Claims, 17 Drawing Sheets

DEVICE AND METHOD FOR EXERCISING EYES

FIELD OF THE INVENTION

The present invention relates to devices and methods for exercising eyes.

BACKGROUND OF THE INVENTION

Vision is the primary navigational system of a human body, providing 80 to 90% of all information received during a person's lifetime. The proficiency of the vision skills affects every human activity and affects human performance on all levels. However, the human vision system functions in a more and more difficult environment as educational and occupational demands continue to grow exponentially in today's society.

The United States economy, as well as that of many foreign countries, have moved from an industrial era to a service era and has entered the information age. More and more, a worker's performance depends on gathering and internalizing a growing body of information in educational, occupational, and even social surroundings.

The computer has become a principal channel for providing services and information. There is an ongoing and dramatic rise in the number of people who use computers at work, at home after work hours, while shopping, reading the newspaper, and the like. The volume of services and information provided via computers also continues to increase. The explosive growth in the use of computers and other vision-related information-gathering activities dramatically increases demands on the vision system.

The visual system and its primary instrument, the eyes, do not respond well to this increased demand. The eyes are meant to respond effortlessly to images of objects that enter awareness and call for attention. However, it is unlikely that the eyes were designed to be used primarily for reading or working on a computer. Yet, as already discussed above, the educational and occupational requirements lead people to do just that.

As a consequence, modern society suffers from a virtual epidemic of vision problems, especially myopia. Such vision problems, including myopia, can be directly related to the amount of time spent reading or working on a computer. The educational system, with its major focus on visual information transmission and communication, is a major contributor to the epidemic.

The eyes are complex neuro-optical systems of the human body. They locate, track, and focus on objects of interest. Before describing the structure and functioning of the eyes, it is useful to describe certain aspects of inanimate optics and related physical phenomena.

A human eye perceives electromagnetic radiation in a certain narrow range of wavelengths (~400 nm to ~700 nm), which may be referred to as the visible range. For the most part, the light perceived by the eye as images of various objects includes mixtures of light waves with different wavelengths. Thus, white light is a mixture of light waves of essentially all wavelengths in the visible range. The electromagnetic waves with unique wavelengths within the visible range (monochromatic light) are perceived as colors. For example, the monochromatic light with the wavelength of 660 nm is perceived as red and the light with the wavelength of 470 nm as blue. Various combinations of light waves (e.g., additions or subtractions) may also be perceived as colors.

On the basis of human perception of colors, the visible range is often divided into various color sub-ranges. One commonly described classification divides the visible range into violet, indigo, blue, green, yellow, orange, and red color sub-ranges:

| Color sub-range | Wavelengths (nm) |
|---|---|
| Violet | ~400–425 |
| Indigo | ~425–450 |
| Blue | ~450–490 |
| Green | ~490–570 |
| Yellow | ~570–590 |
| Orange | ~590–620 |
| Red | >~620 |

Another classification divides the visible range into blue (<~490 nm), green-yellow (~490–590 nm), and red (>~590 nm) sub-ranges. It should be noted that the boundaries between the color sub-ranges are approximate and depend on many factors. For additional discussion of human perception of color, see J. Liberman, Light: *Medicine of the Future,* Bear & Co., 1991.

Light interacts with material substances. Thus, light may change direction when passing through material substances, a phenomenon known as refraction. An index of refraction (n) measures the magnitude of refraction for a given substance. The index of refraction of a substance is the ratio of the velocity of light in a vacuum (C) to the velocity ($\upsilon_v$) of the light wave with a particular wavelength (v) in the substance: $n=C/\upsilon_v$. The velocity of light in a vacuum is constant. However, in material substances, the velocity of light is different for each wavelength v. Therefore, the index of refraction is different at different wavelengths. For this reason, light waves of different wavelengths (colors) are refracted by different amounts through the same optical element. The index of refraction increases as wavelength decreases, and therefore colors of shorter wavelengths exhibit greater change in direction in material substances than colors of longer wavelengths.

The refraction of light is used in various optical systems, such as prisms, lenses, and the like, to manipulate light in a desired manner. A lens is an optical system bounded by two refracting surfaces having a common axis. Lenses refract and focus light emitted by or reflected from various objects. Each lens has a characteristic focus point and focal length, which are commonly used to describe lenses (FIG. 1). The focus point is a point at which the lens focuses light from an object located at an infinite distance from the lens.

Referring to FIG. 1, $F_1$ is the focus point of the lens $L_1$, and $F_2$ is the focus point of the lens $L_2$. The focal length or focal distance (f) is the distance from the center of the lens to its focus point. In the examples of FIG. 1, $f_1$ is the focal length of the lens $L_1$, and $f_2$ is the focal length of the lens $L_2$. The focal length f determines the properties of a lens with respect to focusing of light.

FIG. 2 illustrates how lenses focus light from an object. As seen in FIG. 2, the lens L captures light from an object located at a point Q. The light is focused into an image of the captured object at a point Q'. The point Q is known as the object point and the point Q' as the image point. S denotes the distance from the object point Q to the lens L, and S' denotes the distance from the lens L to the image point Q'.

For an ideal lens, one expression of the relationship between the focal length f and the distances S and S' is the thin lens equation: $1/S+1/S'=1/f$. If the object point Q is located at an infinite distance from the lens L (i.e., S is infinity), the term 1/s approaches zero and the image distance S' is equal to the focal length of the lens L. If the object distance S is less than infinity, the distance S' varies as a function of the distance S. Generally, for a given wavelength, the focal length f is fixed for a given inanimate lens. The term 1/f is also fixed for a given lens. Thus, the term 1/f is a parameter of the functional variation between the terms 1/S and 1/S' (and therefore the distances S and S'). The term 1/f is known as the focusing power of the lens. The focusing power is measured in diopters, which is a metric unit equal to 1 divided by the focal length of the lens, in meters (1 diopter=1 $m^{-1}$). The shorter the focal length f of the lens, the greater the focusing power 1/f.

If the thin lens equation is applied to two different lenses with different focusing powers, the images of objects located at the same distance S are expected to be formed at different image distances S'. Referring again to FIG. 1, the focal length $f_2$ of the lens $L_2$ is greater than the focal length $f_1$ of the lens $L_1$, and thus the lens $L_2$ has more focusing power than the lens $L_1$. As seen from FIG. 1, the greater the focusing power of the lens, the closer to the lens the captured image is formed.

As explained above, the index of refraction (n) varies with the wavelength, and therefore, for the same lens, the magnitude of refraction is different for light of different wavelengths (colors). Thus, the focal length of the same lens is different for different colors. As a consequence, a single lens forms not one image of an object, but a series of images at varying distances from the lens, one for each color present in the light emitted or reflected by the object. If the lens captures monochromatic light, an observer placed at the focus point of the lens perceives the image as sharp. However, if the captured light is not monochromatic, some of the constituent light waves may remain unfocused. This phenomenon, known as chromatic aberration, is illustrated in FIG. 3.

Referring to FIG. 3, the lens L captures non-monochromatic light from an object AB. Suppose, the light from the object AB includes light waves having wavelengths $v_1$ and $v_2$ (light waves $v_1$ and $v_2$), where $v_1<v_2$. Since the index of refraction is greater for shorter wavelengths, the lens L changes the direction of the light wave $v_1$ more than the direction of the light wave $v_2$. Therefore, the focal length of the lens L is smaller for the light wave $v_1$ than for the wavelength $v_2$.

The image for the light wave $v_1$, shown as A'B', is formed closer to the lens L than the image for the light wave $v_2$, shown as A"B". For example, if the wavelength $v_1$ is in the violet color sub-range and the wavelength $v_2$ is in the green color sub-range, the violet image would be formed closer to the lens L than the green image. The variation in the image distance as a function of color is called longitudinal chromatic aberration. The difference in the index of refraction at different wavelengths also affects the size of the image. The variation in the image size as a function of color is known as lateral chromatic aberration. In FIG. 3, the distance a measures the longitudinal chromatic aberration, and the distance b measures the lateral chromatic aberration.

Because of chromatic aberration, the same focus point is not optimal for all colors that comprise the light captured through the lens. Some colors will be perceived as sharp at the focus point of the lens, while others will not. The unfocused colors may form a fuzzy ghost image around the focused image.

As will be explained in more detail in the description of the invention, chromatic aberration may occur in a human eye, which, like inanimate optical systems, includes light-refracting elements. The structure of the eye is schematically illustrated in FIG. 4. Among the major parts of the eye are a cornea 2, an iris 4, a retina 6, an eye crystalline lens 8, a ciliary body 10, and ciliary zonules 12.

The cornea 2 is a transparent membrane that protects the eye from the outside world while allowing light to enter the eye. The iris 4 controls the amount of light that enters the eye by opening or closing a pupil, the variable aperture of the eye. The variations in the size of the pupil allow the eye to function over a wide range of light intensities. Thus, the pupil contracts to limit the amount of light in a bright environment, and fully opens in a dim light. The pupil also contracts for near vision, increasing the depth of field to improve perception of objects located in close proximity to the eyes.

The retina 6 is a thin sheet of interconnected nerve cells, which function as detectors, converting information carried by the light (images) into electrical impulses. The detecting elements of the retina 6 include rods and cones. The cones function primarily in normal lighting condition, while the rods are most effective in dim lighting. The sensitivity of the retina is different for different wavelengths within the visible range. The retina is most sensitive in the middle of the visible range, specifically in the green/yellow color sub-ranges, and least sensitive at both ends of the visible range, namely in the red and blue sub-ranges. The spectral sensitivity is also different for rods and cones. Thus, the peak of spectral sensitivity in normal lighting conditions (cone vision) is approximately 555 nm. In dim lighting (rod vision), the peak of sensitivity is approximately 510 nm. The retina is connected to the optic nerve that carries the information gathered by the eye to the brain. When light enters the eye, the crystalline lens 8 projects an inverted image on the retina 6.

The crystalline lens 8 is a transparent convex-shaped structure that focuses the light entering the eye to form a clear image on the retina 6. If the focus point of the crystalline lens 8 is on the retina 6, the perceived image is sharp. If the focus point is in front of or behind the retina, the sharpness of the image may suffer. The phenomenon of chromatic aberration observed in the inanimate optical systems also occurs in the eye. Nevertheless, in most circumstances, all colors are perceived as sharp to an observer because of various compensating mechanisms of the eye.

The crystalline lens 8 is attached to the ciliary body 10 by way of the ciliary zonules 12. The ciliary body 10 contains a ciliary muscle. The eye crystalline lens 8, the ciliary body 10, and the ciliary zonules 12 work together to keep the images entering the eye in focus.

The ability of the eyes to focus clearly on a target of interest at any distance is called accommodation. It is one of the most important visual skills. Although the thin lens equation (1/S+1/S'=1/f) applies to ideal inanimate lenses, its general principles are helpful to describe the accommodation function of the eye. With respect to the thin lens equation, the focusing power of the eye is 1/f, the distance to an observed target is S, and the distance from the eye lens to the image of the target is S'. As described, an image is sharp if it is focused on the retina. The distance between the crystalline lens and the retina is essentially constant. Thus, the distance S' between the crystalline lens and the image must also be kept essentially constant regardless of the target distance S, which continuously changes as a function of the environment. Applying the thin lens equation, the term 1/S' remains constant, the term 1/S is changing, and therefore, the term 1/f must change with the change in the distance S to maintain the sharpness of the image. The essential mechanism of accommodation therefore involves changing the focusing power of the eye. The smaller the distance to the observed target, the greater the required focusing power of the eye.

A normal eye does not require any increase in the focusing power in order to clearly see a target at 20 feet or beyond. The table below illustrates a useful non-limiting example of the relationship between the distance from an eye to a target of observation and the required focusing power for a normal eye (in diopters):

| Distance (inches) | Required focusing power of a normal eye (diopters) |
|---|---|
| 40 | 1.0 |
| 26 | 1.5 |
| 20 | 2.0 |
| 16 | 2.5 |
| 13 | 3.0 |

Referring to FIG. 4, the change in the focusing power of the eye lens 8 is accomplished by changing the shape of the lens 8 with the help of the ciliary body 10 and the ciliary zonules 12. If the observed target moves closer, the ciliary muscle of the ciliary body 10 constricts thereby causing the zonules 12 to slacken and allowing the crystalline lens 8 to bulge. The resulting increase in the convex cross-section of the crystalline lens 8 increases its focusing power. If the observed target moves away from the eye, the ciliary muscle relaxes, tightening the zonules 12, and flattening the lens 8, thereby reducing the focusing power of a normal eye. At the distance of more than 20 feet, the ciliary muscle is usually relaxed.

In addition to accommodation, other essential visual skills include fixation (the ability to accurately aim the eyes at a target of interest), saccadics (the ability of the eyes to move accurately, efficiently, and rapidly from one target of interest to another), and binocular vision (the ability of the eyes to work together as a team). In large part and for a large proportion of people, inefficiency in any of these essential skills results in visual fatigue and stress associated with visually oriented tasks. It may become difficult for the eyes to aim, move and focus while working as a team, causing discomfort, loss of productivity, and less than optimal educational and/or occupational performance in general. Furthermore, the stress created by the inefficient function of these skills may contribute to the development of eyesight related problems (i.e., myopia, astigmatism). Summarizing, inefficiency in any of the essential visual skills may cause discomfort, loss of productivity, and less than optimal educational and/or occupational performance in general.

To optimize visual functioning and hopefully prevent visual deterioration, the visual system (the eyes, eye muscles and brain centers associated with vision) can be trained to work more efficiently. Vision is a skill that can be trained. The benefits of eye training are multidimensional. Among the benefits, training the eyes provides a physiological improvement in the responsiveness of the entire visual system. The eye muscles, for example, like all trainable muscles improve when properly trained. In effect, they benefit from eye training just as different, more visible human muscles benefit from other forms of exercise.

It is known that physical training improves the ability of the muscular and neurological system to respond with greater speed, accuracy, flexibility and fluidity, thereby enhancing overall performance. The same holds true for training the visual skills required for optimal visual performance. Most of the changes that take place as a function of physical training are gradual and occur over an extended period of time. The same holds true for the eyes. They adapt optimally to exercise that moderately exceeds their capacity.

Therefore, there is a continued and important need for new eye exercise devices and methods. Particularly, there is a need for eye exercise devices that are portable; use moderate levels of exercise, and that may be used to train a variety of visual functions simultaneously.

SUMMARY OF THE INVENTION

The present invention addresses these needs by providing eye exercise devices and methods that use the eye's natural response to different colors to train the eye(s). In accordance with one aspect, the invention provides an eye exercise device that includes a) a housing, including a plurality of colored light sources viewable by an observer and disposed in a substantially linear alignment, the colored light sources being of at least two different colors, including a first color which causes the eye to increase the focusing power of the eye to gain a sharp image of the first color, and a second color which causes the eye to decrease the focusing power of the eye to gain a sharp image of the second color; and b) a controller for controlling the display of the light sources to an observer.

Preferably, the light sources of the first color are mounted in an alternating arrangement with the light sources of the second color. Preferably, the first color is selected from the group consisting of orange and red, and the second color is selected from the group consisting of violet, indigo, turquoise, and blue. The more preferred first color is red, and the more preferred second color is blue or violet. The preferred light sources are light emitting diodes.

The device may further include eyeglasses having interchangeable red and blue or violet filters for selectively affecting the display of the light sources. The device may also further include a control panel for adjustment of the controller.

In accordance with one embodiment, the housing is a horizontal bar, and the eye exercise device further includes a handle connected between two ends of the horizontal bar, dividing the horizontal bar into two segments, each of the segments extending from one of the ends of the horizontal bar to the location where the handle is connected. The horizontal bar has a top surface and a bottom surface. The top surface houses the light sources. The top surface of the horizontal bar may also include a linear marking extending substantially between the ends of the horizontal bar. The handle is connected to the horizontal bar from the bottom surfaces side. The preferred shape of the handle allows placement of the device in a vertical, oblique, or horizontal position with respect to a horizontal plane without additional structural elements. The preferred shape of the handle is octagonal. Also, preferably, at least one of the ends of the horizontal bar defines an open recess that is used in some of the eye exercises.

In a more preferred embodiment, the horizontal bar is foldable so that the eye exercise device may be placed in an operational position, in which the horizontal bar is substantially perpendicular to the handle, or a storage position in which the horizontal bar is folded and the two segments of the bar are substantially parallel with and laying adjacent to the handle. Preferably, the location where the handle is connected to the horizontal bar is substantially equidistant from both ends of the horizontal bar. Preferably, the light sources are also substantially equidistant from each other.

In accordance with another aspect, the invention provides an eye exercise device that includes a) one or more first light sources of a first color that causes the eye to increase the focusing power of the eye to gain a sharp image of the first light sources, b) one or more second light sources of a second color that causes the eye to decrease the focusing power of the eye to gain a sharp image of the second light sources, the second color being different from the first color, c) a housing to which the first and second light sources are mounted, and d) a programmable controller to alternate the display of the first and second light sources to exercise one or more eyes of a person by alternately causing an increase and decrease in the focus power of an eye of a human subject observing the light sources.

Preferably, the first color is selected from the group consisting of orange and red, and the second color is selected from the group consisting of violet, indigo, turquoise, and blue. The preferred first color is red, and the second color is blue or violet. In this aspect, the eye exercise device may include any of the specific features previously described above in reference to another device aspect of the invention.

According to another aspect, the invention provides a method of exercising an eye of a person that includes a) exposing the observer to a predetermined arrangement of (i) one or more first light sources of a first color that causes the eye to increase the focusing power to gain a sharp image of the first light sources, and (ii) one or more second light sources of a second color different than the first color that causes the eye to decrease the focusing power to gain a sharp image of the second light sources; and b) alternating the display of the first and second light sources to exercise the eye of the observer observing the light sources by alternately causing the focusing power to increase and decrease.

Preferably, the alternating includes alternating the display between the first color being selected from the group consisting of orange and red and the second color being selected from the group consisting of violet, indigo, turquoise, and blue. The preferred first color is red, and the preferred second color is blue or violet. The preferred pre-determined arrangement is a substantially linear alignment of the light sources.

In accordance with this aspect of the invention, the method further includes positioning the observer vertically in front of the substantially linear alignment of the light sources during the exercise. Preferably, the light sources and the eyes of the observer are at approximately the same level. The observer may wear eyeglasses having interchangeable red and blue or violet filters to selectively affect the display of the light sources to the observer.

In one embodiment of this aspect of the invention, the method further includes placing the light sources in such a manner that a vertical plane containing the substantially linear alignment of the light sources and a vertical plane containing an imaginary line drawn through the eyes of the observer are substantially parallel to each other. The substantially linear alignment of the light sources may be placed in a horizontal, oblique, or vertical position with respect to a horizontal plane containing the eyes of the observer. Once the observer and the light sources are situated as desired, the observer is exposed to a discreet exercise sequence. Thereafter, the distance between the observer and the light sources may be changed, and the observer may be exposed to another discreet exercise sequence. During the exercise, the light sources are preferably activated consecutively and one at a time.

In another embodiment of this aspect of the invention, the method further includes placing the light sources in such a manner that a vertical plane containing the substantially linear alignment of the light sources and a vertical plane containing an imaginary line drawn through the eyes of the observer are substantially perpendicular to each other. Preferably, the method further includes activating the light sources consecutively and one at a time.

In accordance with another aspect, the invention provides a method of exercising an eye or eyes of an observer, including a) exposing the observer to a plurality of red and blue light sources, and b) activating one or more of the light sources to display the light sources to the observer one-at-a-time.

Preferably, the light sources are in a substantially linear alignment. Also, the red light sources and the blue light sources are preferably mounted in an alternating arrangement with each other. In the preferred embodiment, the light sources are displayed sequentially.

In both method aspects of the invention, it is preferred to use the eye exercise devices described herein. The features, embodiments, or aspects of the eye exercise devices are suitable for use with the methods of the invention.

In accordance with another preferred aspect, the invention provides a kit for exercising eyes including a) a device that includes a plurality of colored light sources viewable by an observer and disposed in a substantially linear alignment, the colored light sources being of at least two different colors, including a first color which causes the eye to increase its focusing power to gain a sharp image of the first color and a second color which causes the eye to decrease its focusing power to gain a sharp image of the second color; and b) eyeglasses having interchangeable color filters of the first color and second color for selectively affecting the display of the light sources to the human subject.

Preferably, the light sources of the first color are mounted in an alternating arrangement with the light sources of the second color. Preferably, the first color is selected from the group consisting of orange and red, and the second color is selected from the group consisting of violet, indigo, turquoise, and blue. The more preferred first color is red, and the more preferred second color is blue or violet.

DESCRIPTION OF PREFERRED EMBODIMENTS

Figure 1:
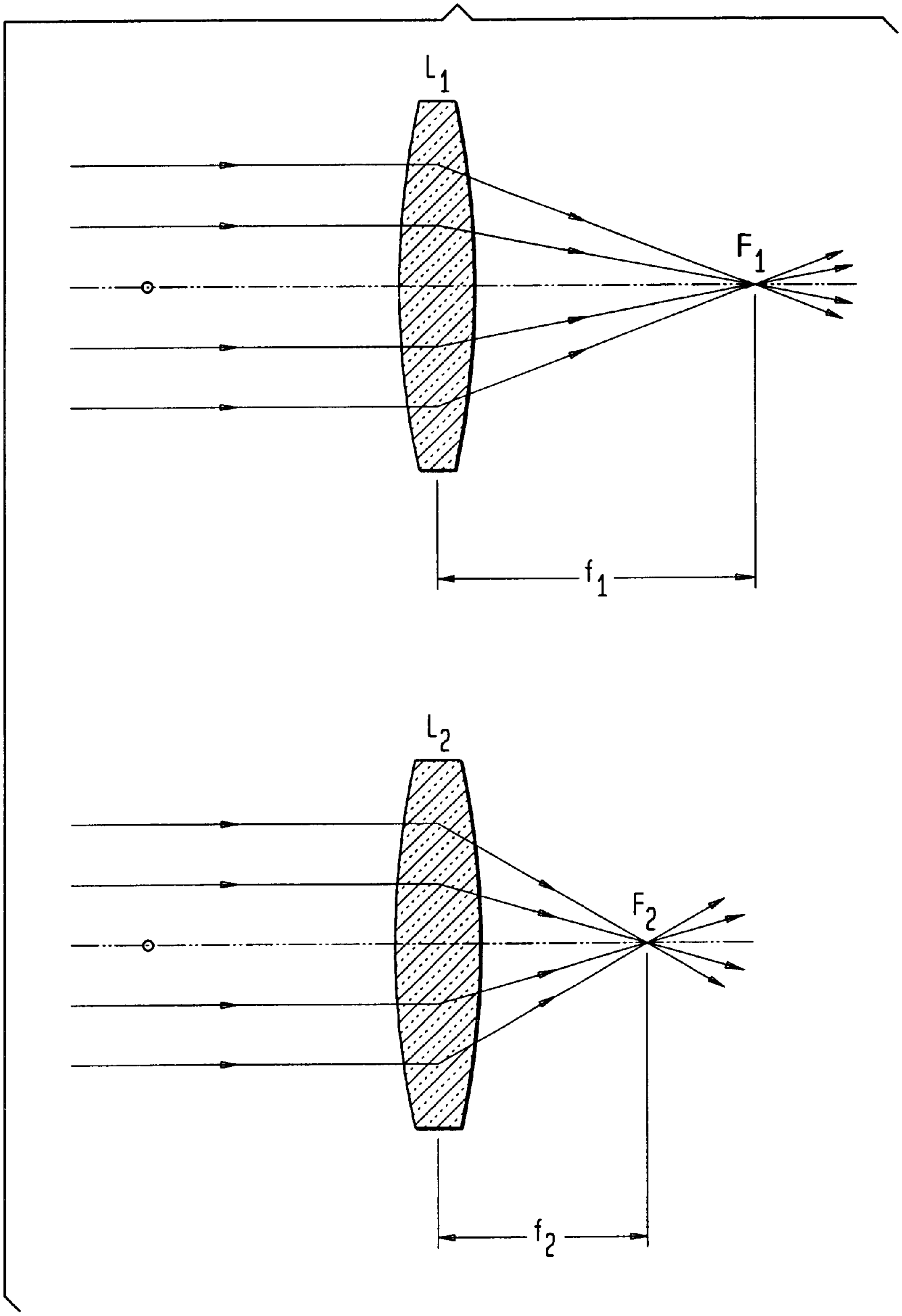
FIG. 1 illustrates characteristics of lenses, such as focus point and focal length.
Figure 2:
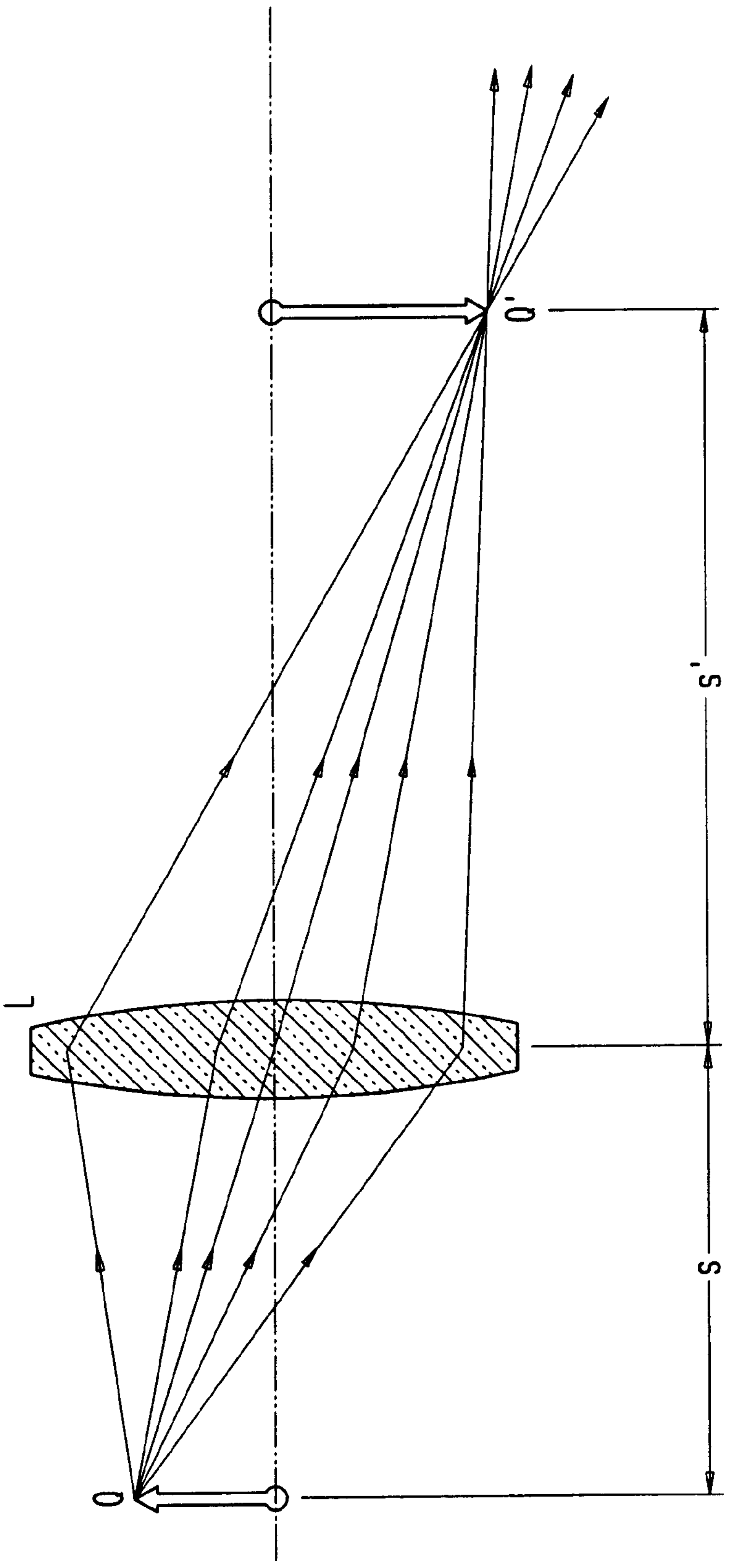
FIG. 2 illustrates focusing of object images by lenses.
Figure 3:
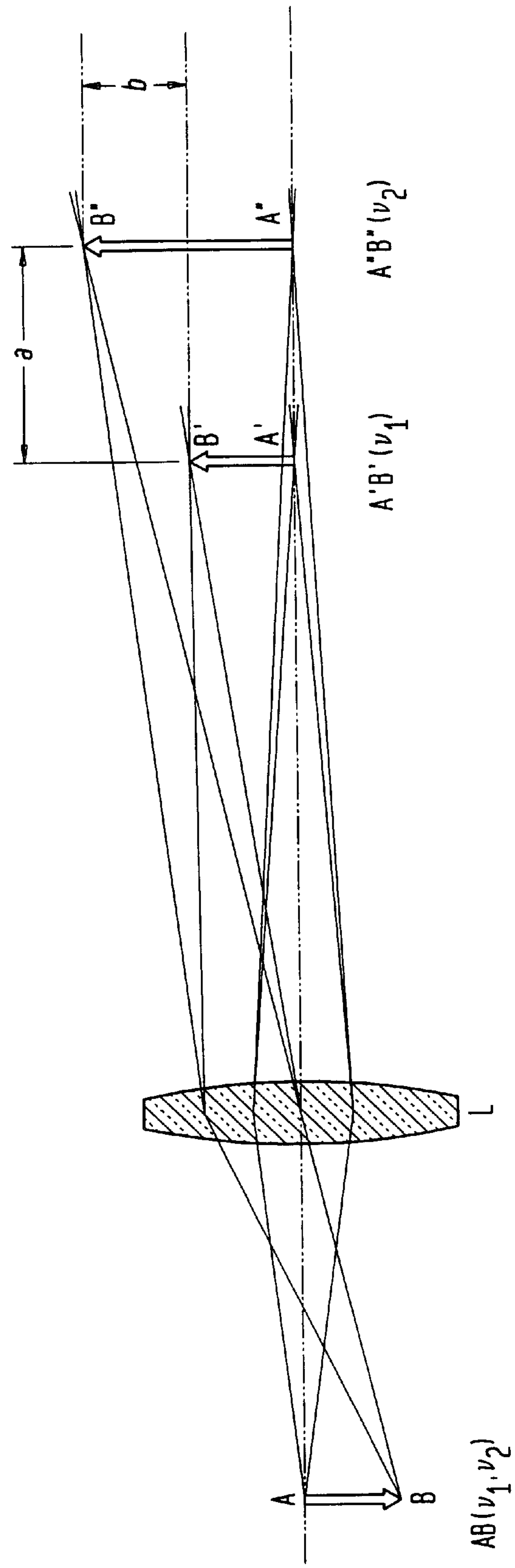
FIG. 3 illustrates chromatic aberration in inanimate lenses.
Figure 4:
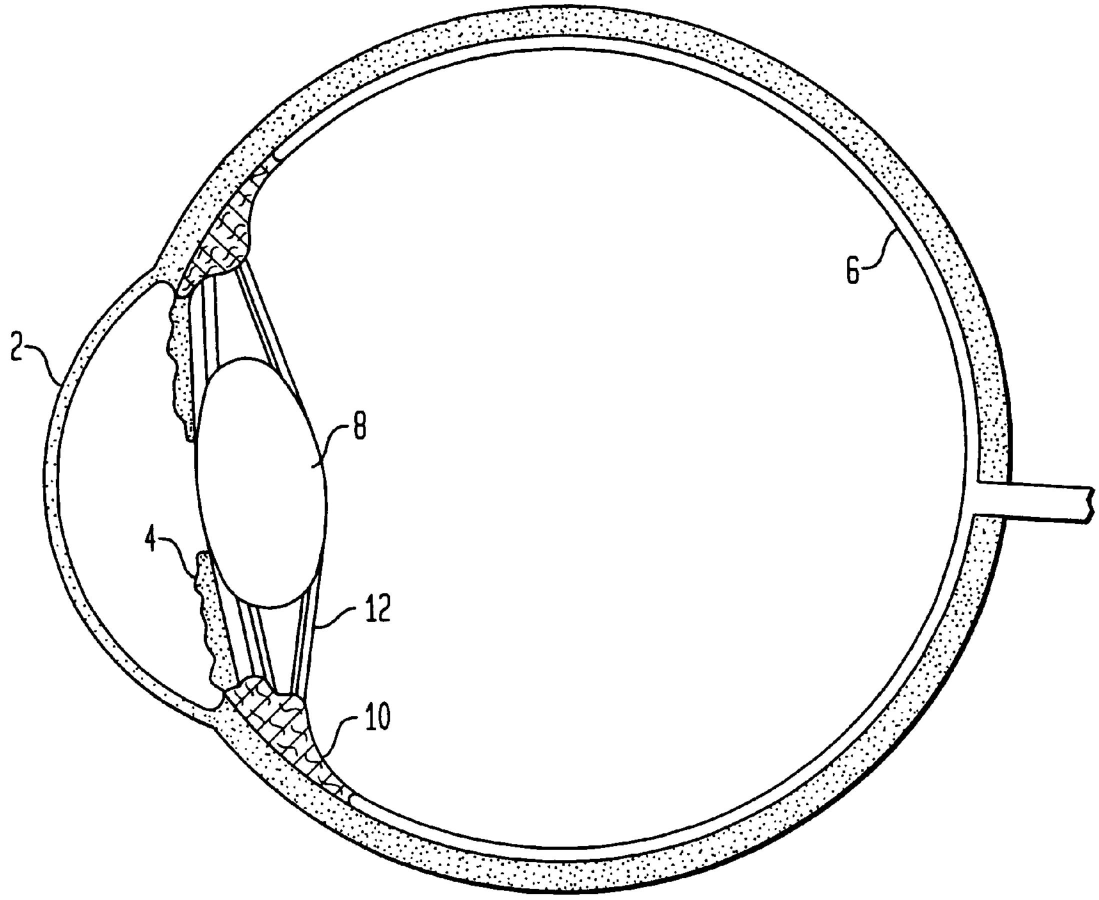
FIG. 4 is a schematic cross-sectional view of a human eye.
Figure 5:
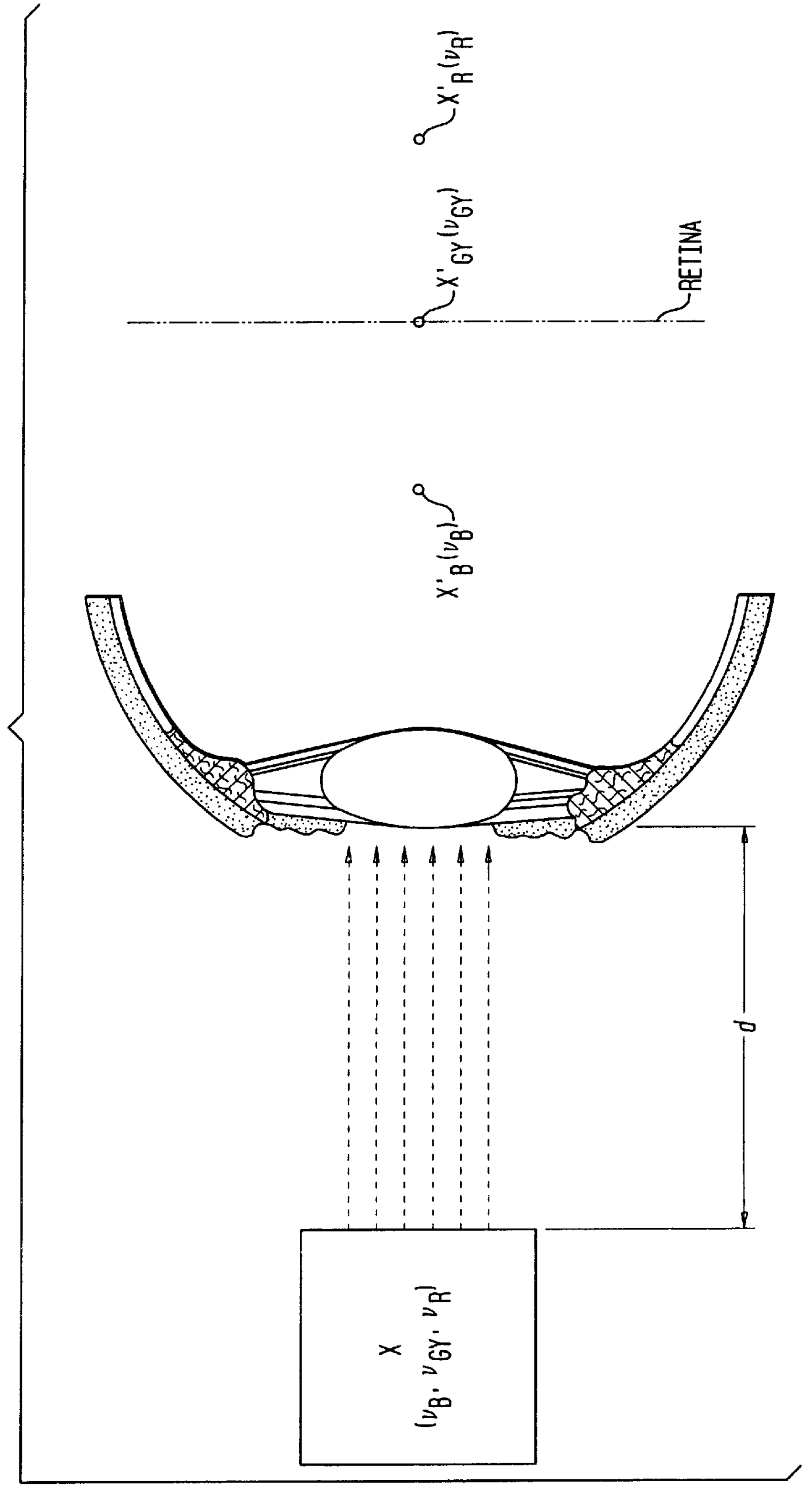
FIG. 5 illustrates longitudinal chromatic aberration in a human eye.

While the invention is by no means limited to any specific theory, the inventor recognized that chromatic aberration of the eye might be utilized in exercising the eye(s). Suppose, the eye observes an object X having a full color spectrum (FIG. 5). The object X reflects or emits light waves of substantially all wavelengths of the visible range, including a light wave of the wavelength $\nu_B$ in the blue color sub-range (the light wave $\nu_B$), a light wave of the wavelength $\nu_{GY}$ in the green-yellow color sub-range (the light wave $\nu_{GY}$), and a light wave with the wavelength $\nu_R$ in the red color sub-range (the light wave $\nu_R$). Because of the different refractive indexes ($n(\nu_B)>n(\nu_{GY})>n(\nu_R)$), the light of longer wavelengths (e.g., $\nu_R$) penetrates deeper into the eye than the light of shorter wavelength (e.g., $\nu_B$). The light waves $\nu_B$, $\nu_{GY}$, and $\nu_R$ focus as images $X'_B$, $X'_{GY}$, and $X'_R$, respectively, at different distances from the eye lens, resulting in a longitudinal chromatic aberration of the eye lens.

Figure 6:
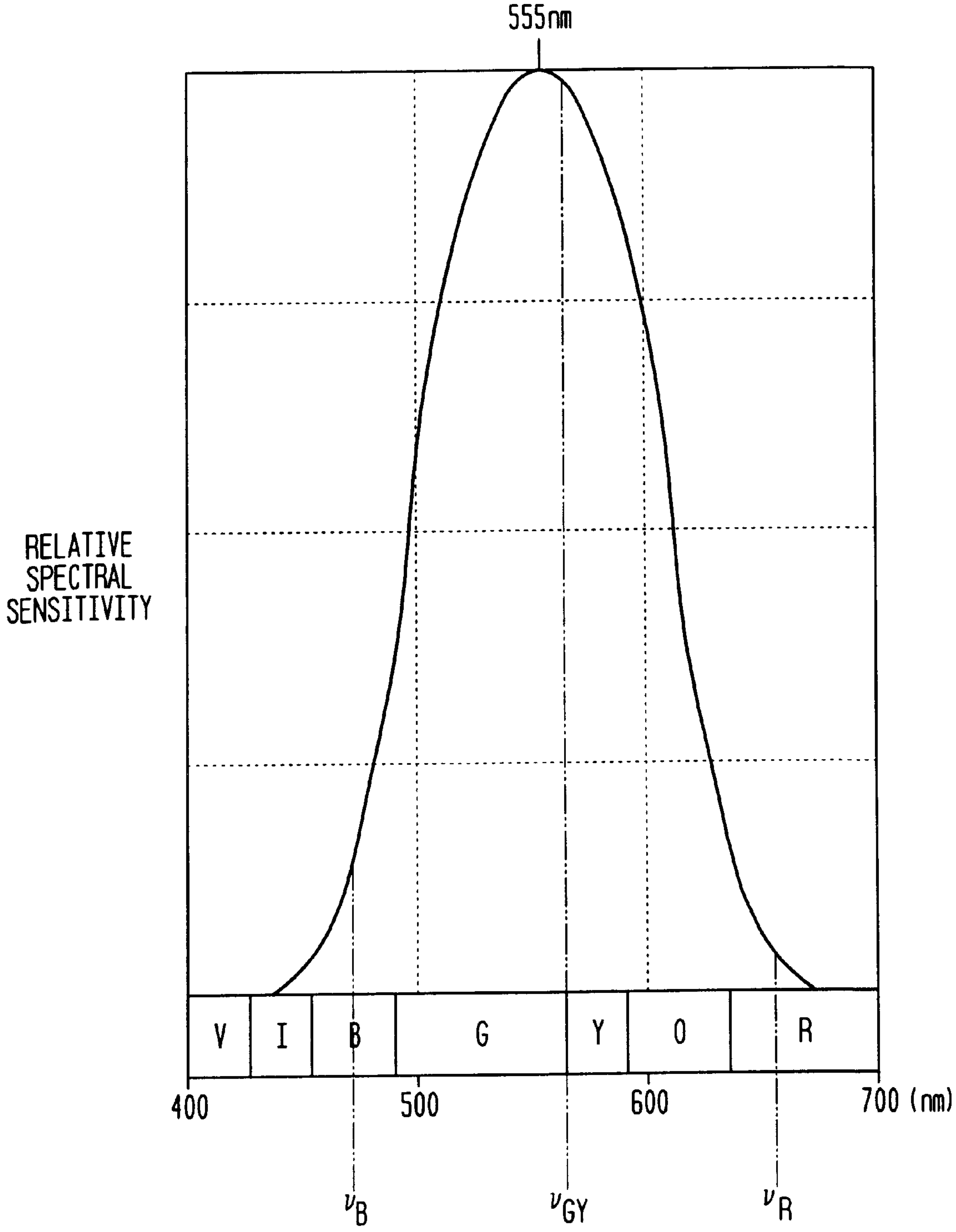
FIG. 6 shows an approximation of the relative spectral sensitivity curve of the retina in normal lighting conditions.

As seen in FIG. 5, the optimal focusing powers for the light waves $\nu_B$, $\nu_{GY}$, and $\nu_R$ are different because of the longitudinal chromatic aberration. The blue image $X'_B$, the green-yellow image $X'_{GY}$, and the red image $X'_R$ cannot be focused on the retina at the same time. For the full color object X, the eye adjusts its focusing power to focus the light wave for which the retina has greatest spectral sensitivity. FIG. 6 shows the relationship between the wavelength and sensitivity of the retina (the relative spectral sensitivity curve) in normal lighting conditions (V denotes violet, I denotes indigo, B denotes blue, G denotes green, Y denotes yellow, O denotes orange, and R denotes red color sub-ranges). Referring to FIG. 6, the sensitivity of the retina for the light wave $\nu_{GY}$ is dramatically greater than for the light waves $\nu_B$ and $\nu_R$. In other words, the retina detects substantially more light at the wavelength $\nu_{GY}$ than at the wavelengths $\nu_B$ or $\nu_R$. For this reason, while observing the full color spectrum object X, the eye adjusts the focusing power to focus the image $X'_{YB}$ on the retina (FIG. 5). The blue image $X'_B$ focuses in front of the anterior surface of the retina, and the red image $X'_R$ focuses behind the anterior surface of the retina.

Figure 7A:
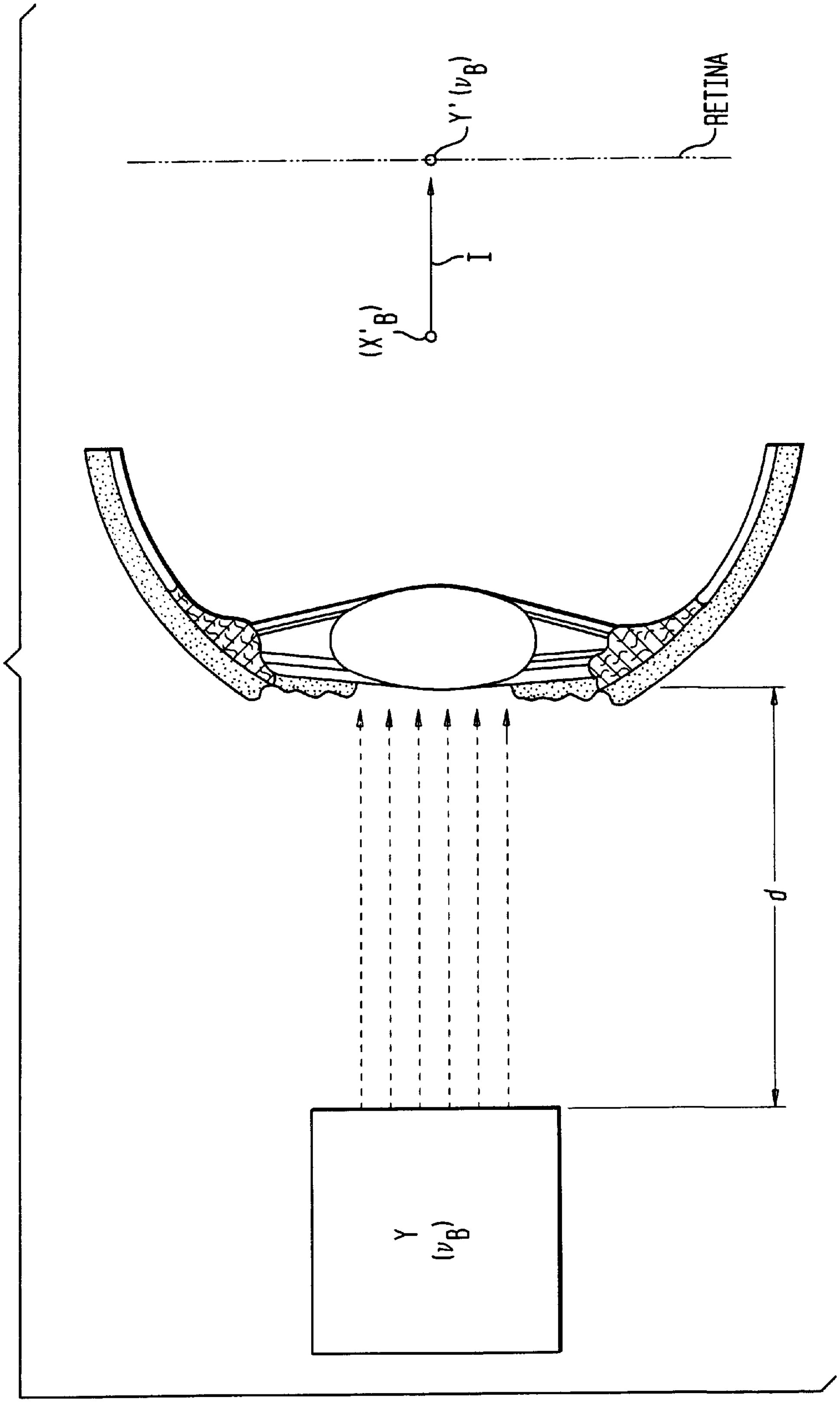
FIGS. 7A–7B illustrate adjustment of eye's focusing power due to chromatic aberration.
Figure 7B:
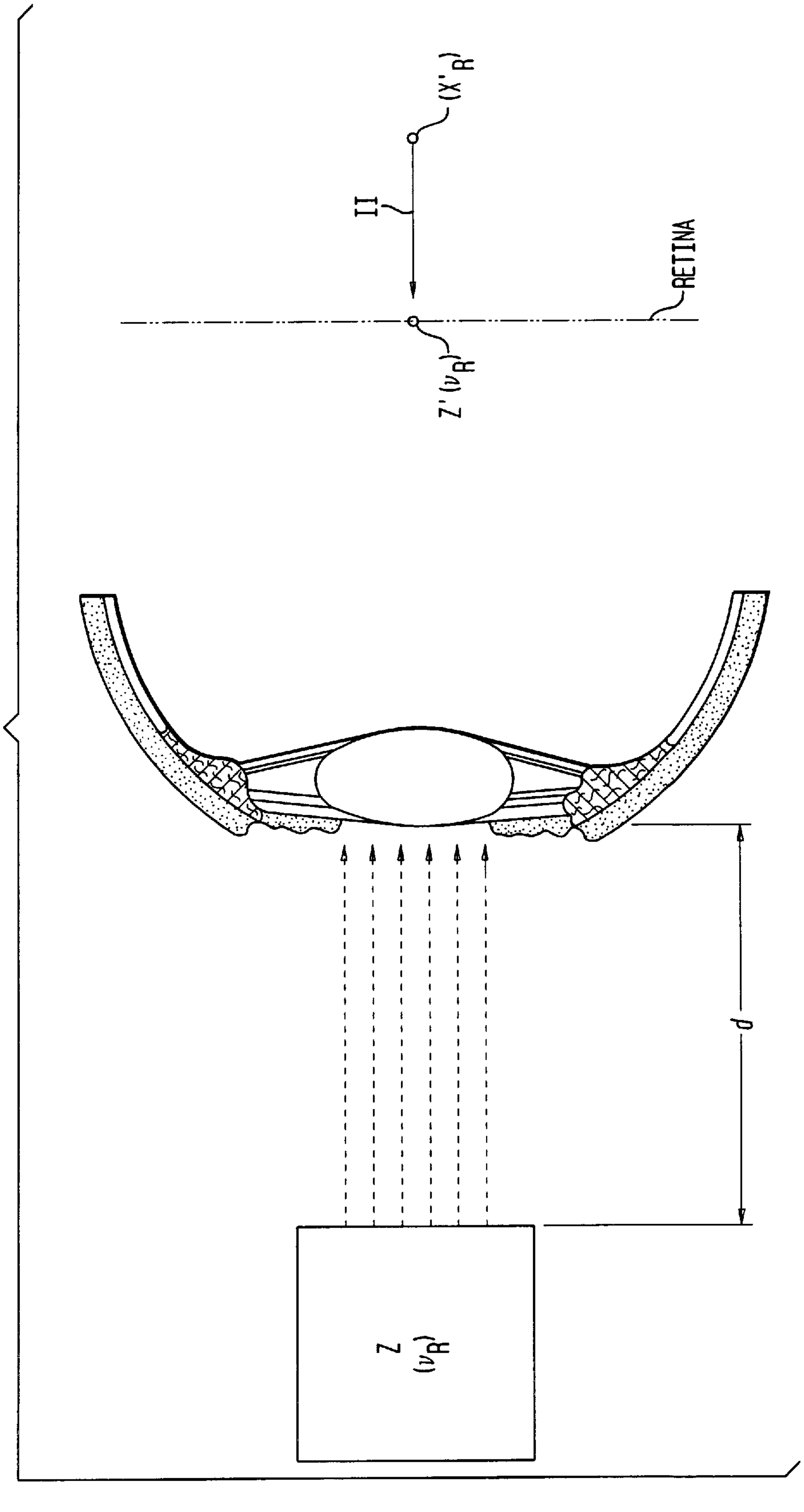

Suppose, the object X is replaced with an object Y that emits or reflects only the blue light wave $\nu_B$, producing a blue image Y' (FIG. 7A). It is no longer necessary to maintain the focusing power that was suitable for the object X. At the focusing power optimal for the object X, the blue image ($X'_B$) was located in front of the retina. To focus the image Y' on the retina, the eye decreases the focusing power relative to the focusing power for the object X (shown by the arrow I). If instead of the blue object Y, the object X is replaced with a red object Z (FIG. 7B) that emits or reflects only the red light wave $\nu_R$, the eye increases the focusing power relative to the focusing power for the object X (shown by arrow II). The adjustments in the focusing power are believed to occur automatically.

Thus, in accordance with the preferred aspect of the invention, the eye may be exercised by alternate exposure to light of a color(s) that includes the wavelength(s) $\nu_a$, and a color(s) that includes the wavelength $\nu_b$ shorter than $\nu_a$, where $\nu_a$ and $\nu_b$ are different from each other. Alternate exposure to colors of the different wavelengths $\nu_a$ and $\nu_b$ causes the eye to alternately increase and decrease its focusing power to maintain the sharpness of perception. It is believed that, in response to such alternating exposure, the ciliary muscle acts in the opposite directions, resulting in a gentle rocking motion that moderately exerts and exercises the eye muscles. The focusing and aiming mechanisms of the eye are alternately stimulated and relaxed, training the eye in a natural way without using external lenses and prisms. The neural functions associated with the visual skills, including the brain, are also trained.

The greater the difference between the wavelengths of the first and second colors, the greater is the magnitude of the focusing power adjustment. Therefore, preferably, the difference $\Delta\nu$ ($\nu_a-\nu_b$) between the wavelengths $\nu_a$ and $\nu_b$ is maximized. The greater is $\Delta\nu$, the greater the training effect. The colors of wavelengths close to the peak of spectral sensitivity curve are preferably excluded when the observer is exposed to colors $\nu_a$ and $\nu_b$.

Preferably, if $\nu_0$ is the wavelength at which a normal eye has a peak of spectral sensitivity in normal lighting conditions, $\nu_a$ is longer than $\nu_0$, and $\nu_b$ is shorter than $\nu_0$. If $\nu_0$=555 nm, the focusing power of a normal eye required to gain a sharp perception of a color with a wavelength of 555 nm in normal lighting conditions at a given distance d may be defined as the mean eye focusing power. The mean focusing power divides the visible range into two color groups for the purposes of the present invention. The first group of first colors include colors that, when observed at the distance d, require the eye to increase the focusing power with respect to the mean focusing power to gain a sharp image of the first colors. The second group (or second colors) include colors that, when observed at the distance d, require the eye to decrease the focusing power with respect to the mean focusing power to gain a sharp image of the second color. Pure monochromatic colors or colors comprising mixtures of wavelengths may be used. Examples of first colors include orange and red. Examples of second colors include violet, indigo, turquoise, and blue. In the methods and devices of the present invention, the preferred first color is red, and the preferred second colors are blue and violet. Red and blue or violet light waves have wavelengths at the opposite ends of the visible light range. For this reason, it is believed that the training effect of alternate exposure to red and blue or violet colors is greater than for other color pairs.

Preferably, an observer is alternately exposed to colors of first and second groups. For example, the observer may be exposed to blue color, followed by red color, followed by blue color, and so on, with the exclusion of the green or yellow colors from the environment and the target of observation. However, the colors with high spectral sensitivity may also be included in the exposure sequence. An example of such sequence is blue, green, red, green, blue, and so on.

The focusing power of the eye depends both on the color and the distance to the target. Thus, preferably, the spatial location of the alternately displayed colors is changing simultaneously with the alternate change of colors. The change in the spatial location trains the aiming mechanism of the eyes. Preferably, the methods and devices of the invention involve exposure to colored objects, more preferably, colored light sources.

Figure 8A:
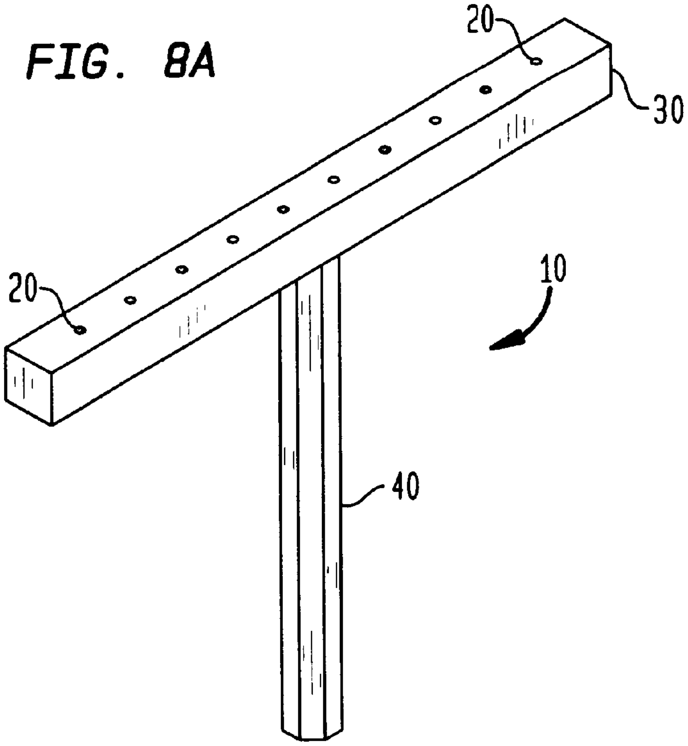
FIGS. 8A–8B show an eye exercise device in accordance with the preferred aspect of the invention.
Figure 8B:
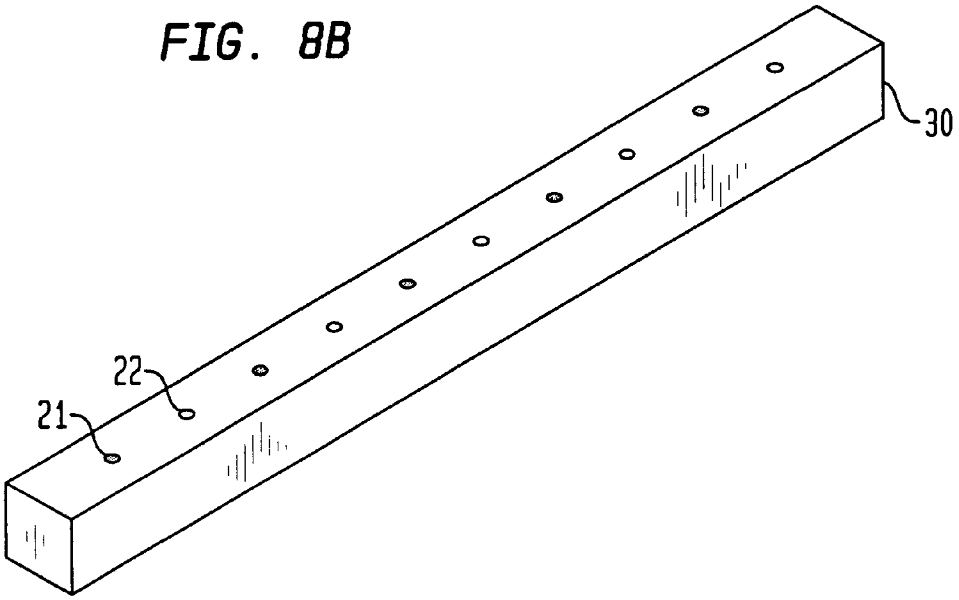

FIGS. 8A and 8B show the preferred eye exercise device in accordance with the present invention. It should be understood that the specific embodiments are described below for the purpose of illustration only. The major components of the device 10 are a plurality of colored light sources 20, a housing 30, and a handle 40 (FIG. 8A). The handle 40 supports the housing 30. Preferably, the handle 40 has squire or octagonal shape. As seen from FIG. 8A, the housing 30 supports or houses the colored light sources 20 in a substantially linear alignment. Other arrangements of the light sources are also possible although the linear alignment is preferred.

The colored light sources 20 preferably include light sources 21 of the first color(s), and light sources 22 of the second color(s) (FIG. 8B). The preferred first color is red, and the preferred second color is blue or violet. The preferred light sources are light emitting diodes (LEDs).

Preferably, the light sources 21 and 22 are arranged in an alternating pattern to each other. Non-limiting examples of such patterns are shown in the table:

| Color(s) of the light sources 21 | Color(s) of the light sources 22 | Total number of light sources | Pattern* |
|---|---|---|---|
| R | B | 12 | R, B, R, B, R, B, R, B, R, B, R, B |
| R | V | 6 | V, R, V, R, V, R |
| R | B, V, T, I | 10 | R, V, R, I, R, B, R, T, R, V, R, B |
| R | B | 9 | B, R, B, R, B, R, B, R, B |

*R denotes red, B denotes blue, V denotes violet, T denotes turquoise, I denotes indigo.

In operation, the subject/observer is placed in front of the device 10, with the device 10 set up in a desired orientation with respect to the observer. For example, the light sources 20 may be placed at, above or below the eye level of the observer, or at an angle to the eyes of the observer. Also, the device 10 may be set up with the colored light sources 20 located horizontally, vertically and/or obliquely relative to the observer. The device housing 30 of the device 10 may also extend perpendicularly away from the observer's nose.

Then, the person controlling the device 10 (e.g., the observer) activates the device, selects the exercise program, and initiates the desired exercise. During the exercise, one or more of the plurality of colored light sources 20 are illuminated for display in the manner selected by the user, for example, sequentially left to right and back right to left, sequentially right to left, randomly, and so on. The light source is "displayed" when it is actuated (turned on) at a given moment of time. The colored light sources 20 may be displayed simultaneously, one at a time, or in other desired ways and sequences. Preferably, the light sources 20 are displayed sequentially one at a time. More preferably, the first light sources are displayed alternately with the second light sources. For example, a blue light source is displayed, followed by a red light source, followed by a blue light source, and so on. The light sources 20 are arranged in an alternating pattern, and therefore sequential, one-at-a-time display alternately displays light sources 21 and 22. In accordance with the preferred embodiment, during the eye exercise, the subject observes and focuses on each light source as it is displayed.

Figure 9A:
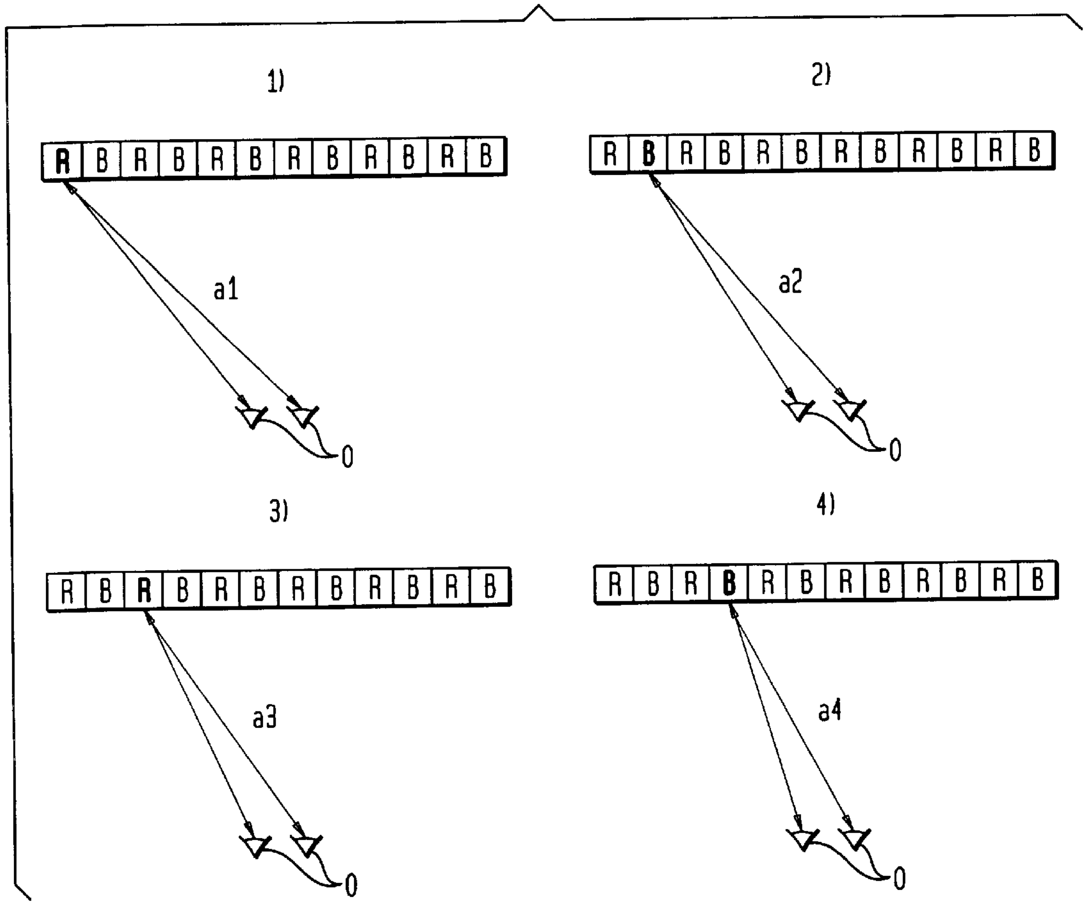
FIGS. 9A–9B illustrate examples of eye exercises in accordance with one embodiment of the invention.
Figure 9B:
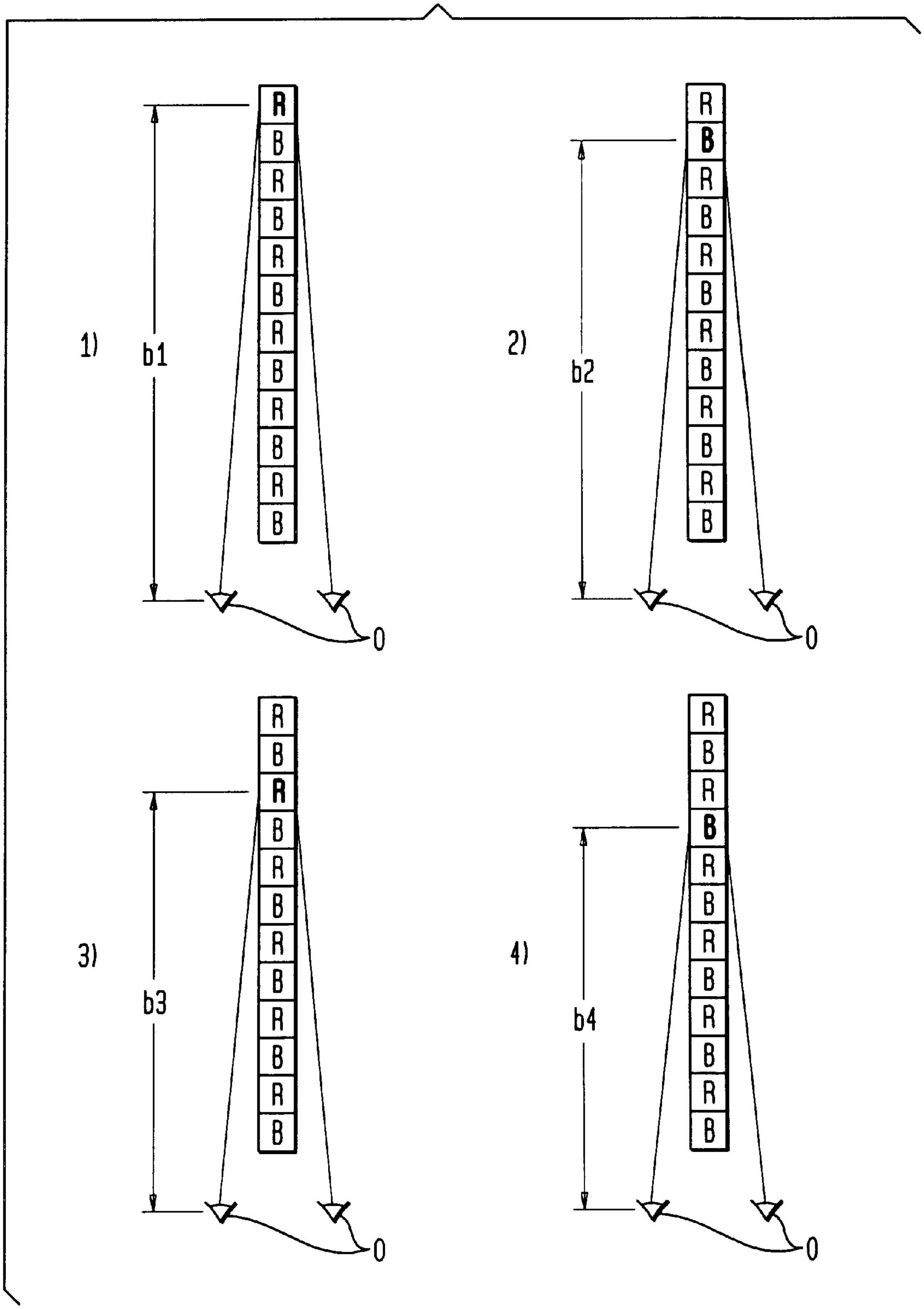

FIGS. 9A and 9B illustrate non-limiting examples of the training exercises with the device having six red and six blue light sources arranged in a R,B,R,B,R,B,R,B,R,B,R,B pattern. O denotes the observer, and the displayed light sources are shown in bold. In the exercises illustrated in FIG. 9A, the light sources are set up in a plane parallel to the observer's eyes, and displayed one-at-a-time from left to right. At the time 1, the observer perceives a red light source at a distance a1, at the time 2, a blue light source at a distance a2, at the time 3, a red light source at a distance a3, and so on. Thus, both the color and the distance to the target of observation (the displayed light source) change during the exercise. As described, the eye adjusts its focusing power in response to both change in color and distance. The location of the displayed light source in the horizontal plane relative to the observer is also changing, exercising the ability of the observer's eyes to move freely and accurately in the horizontal plane as the eyes track the movement of the displayed light source.

In the exercise shown in FIG. 9B, the light sources are placed perpendicularly to the observer. At the time 1, the observer perceives a red light source at the distance b1, at the time 2, a blue light source at the distance b2, and so on. As in the exercise shown in FIG. 9A, both the color of the displayed light source and the distance change. The change in the distance (e.g., from b1 to b2) is larger. In this exercise, the eyes also converge more or less as the target of observation moves closer or further, exercising the ability of the eyes to work together as a team. The use of different exercises available with the device 10 allows the simultaneous training of a variety of different visual skills under different conditions.

Figure 10A:
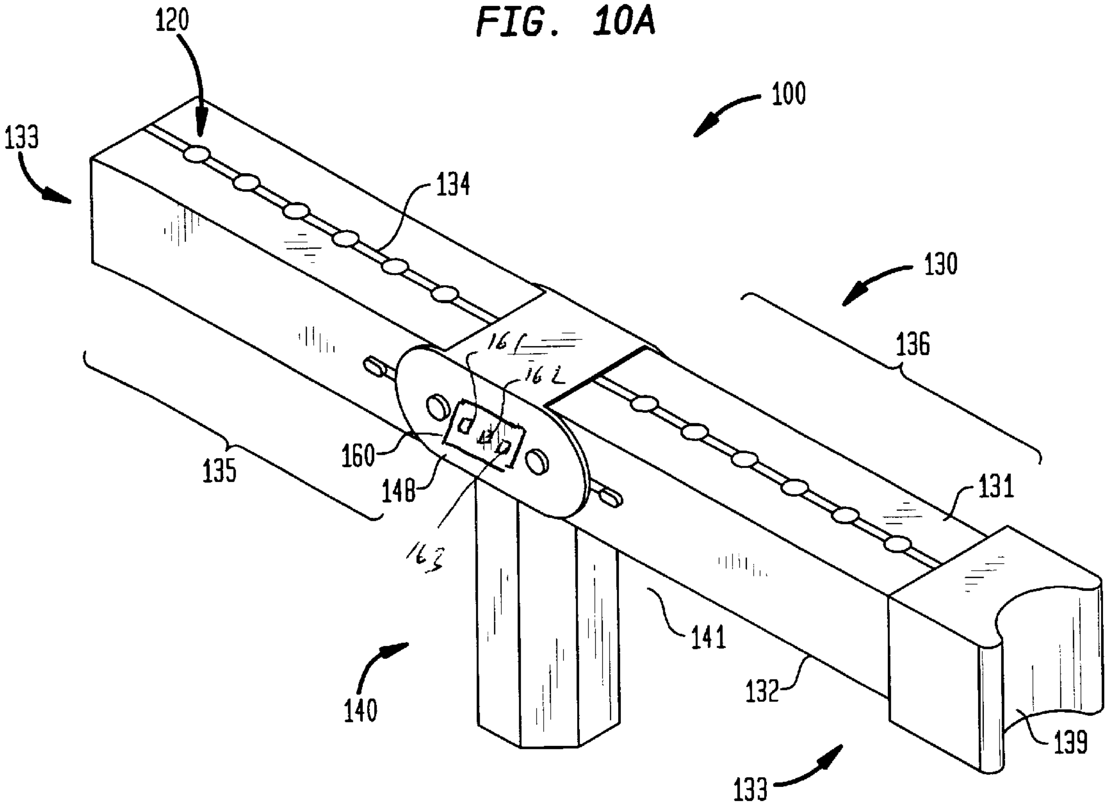
FIGS. 10A–10B show a preferred embodiment of the eye exercise device in accordance with the invention.
Figure 10B:
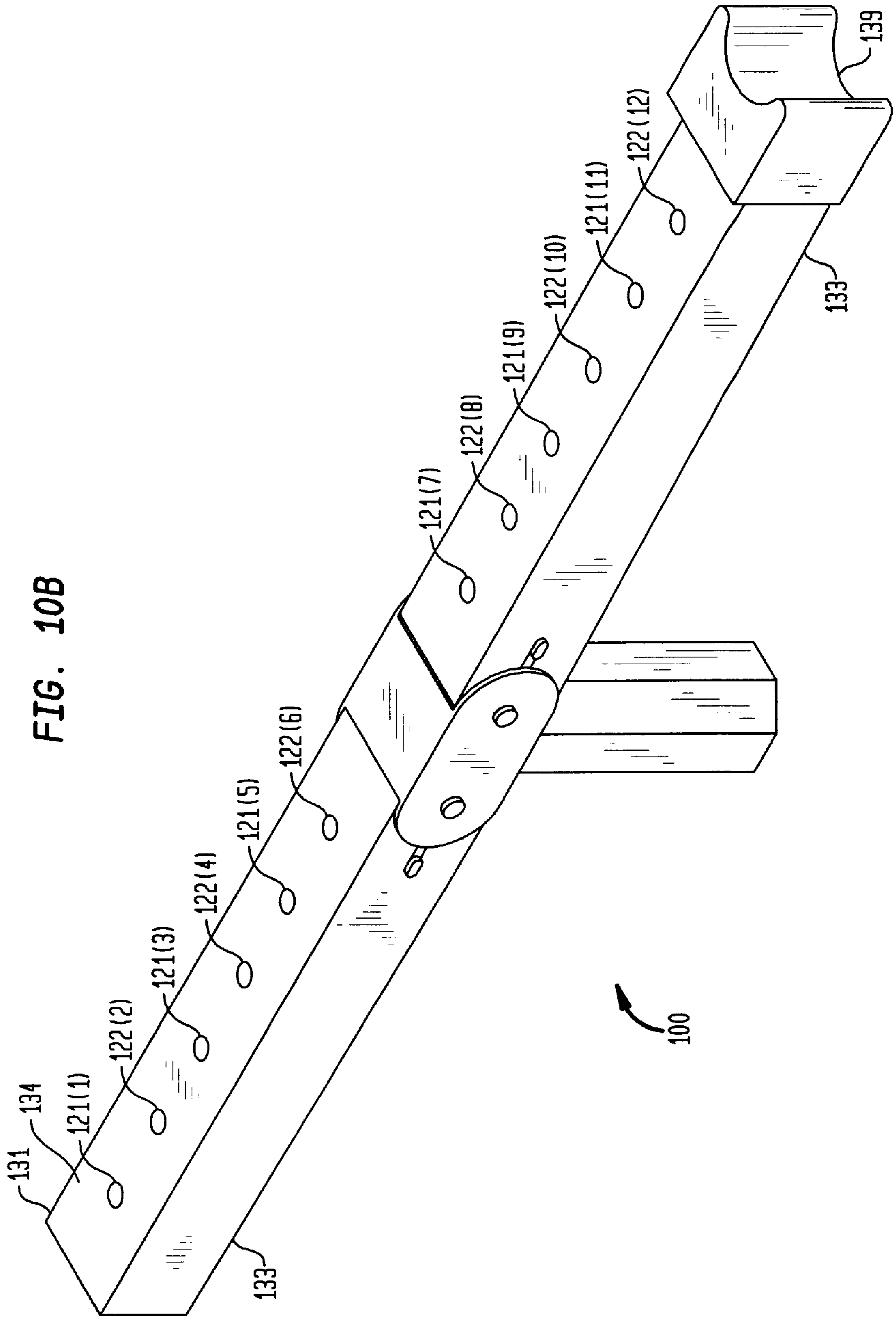

In the preferred embodiment, the invention provides a portable eye exercise device 100 shown in FIGS. 10A–10B. The device 100 is foldable for convenient use, and may be used at home, while traveling, and the like. The device 100 is intended primarily for personal use, without professional assistance.

As seen from FIG. 10A, the device 100 includes a plurality of LEDs 120, a foldable horizontal bar 130, a handle 140, a control panel 160, a display panel 169 (not shown), and a controller 170 (not shown). The horizontal bar 130 has a top surface 131 and a bottom surface 132 (FIG. 10B). Red LEDs 121 and blue LEDs 122 are mounted on the top surface 131 in an alternating arrangement. Each LED may be referred to using numbers from (1) to (12). A linear stripe 134 extends between ends 133 of the horizontal bar 130. One of the ends 133 defines a recessed bridge 139, which is used in some eye exercises to ensure appropriate position for the person using the device 100. A proximate end 141 of the handle 140 is connected to the bar 130 at a connection location 148, which divides the bar 130 into a right segment 135 and a left segment 136. When the device 100 is used for eye exercises, both segments are unfolded (FIG. 10A). If the device 100 is not in use, the segments 135 and 136 may be folded along the handle 140 for easy storage.

In a preferred variant, the device 100 is a compact, hand-held unit. For instance, the horizontal bar may be 36" long, the handle may be 4" long and the LEDs are located 2.75" apart. The handle may be in the octagonal or other similar form that allows placement of the device in horizontal or vertical orientation without additional support or attachments. When folded for storage, the device is 15–16"

in length and 5–6" thick. The size of the device may be further minimized if desired.

Figure 11:
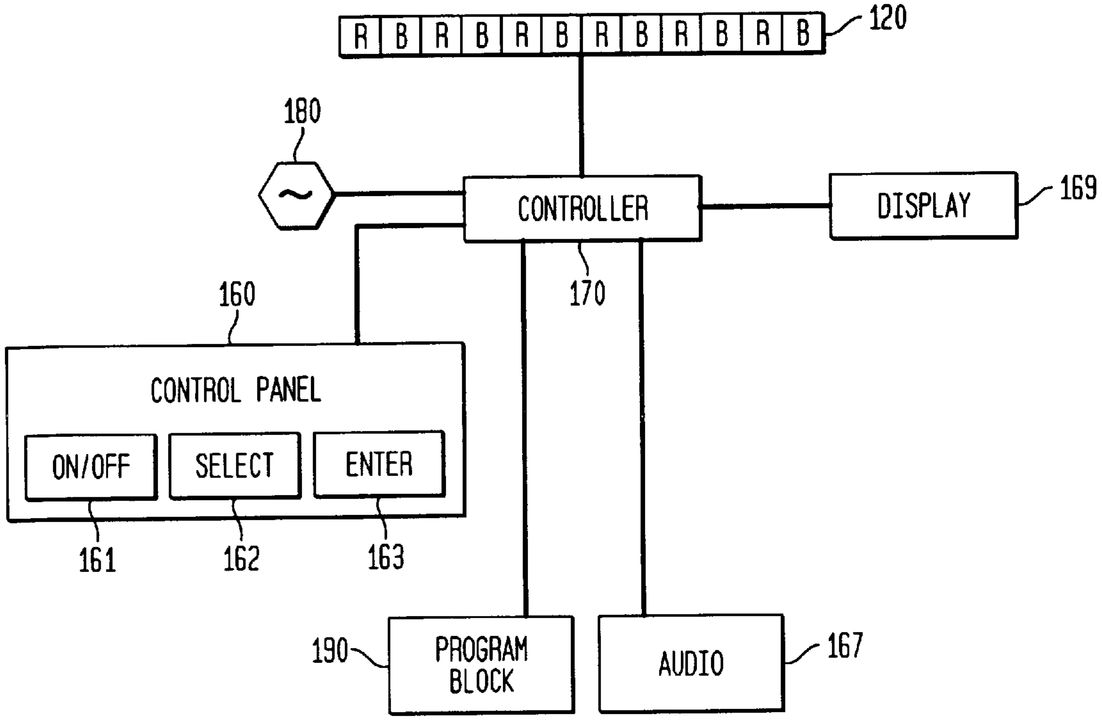
FIG. 11 is a block functional diagram of the eye exercise device in accordance with the preferred embodiment of the invention.

FIG. 11 shows a functional block diagram of the device 100. The controller 170 guides the manner and order of display of the LEDs 120. The controller 170 may be mounted within the horizontal bar 130 or any other portion of the device 100. The LEDs 120 are connected to a source of power 180 through the controller 170. The controller 170 is also connected to the control panel 160, a program block 190, a display 169, and an audio signaling device 167. The controller 170 can comprise a special purpose controller or a general-purpose microprocessor programmed to control the function of the device 100. Any connections, blocks and/or components known in the art may be used to effect the operation of the device 100.

The program block 190 can comprise a memory, which stores instructions for execution by the controller 170, including various pre-set exercise sequences. The display 169 displays the status of an exercise, speed setting, pre-set exercise ID, and the like. For example, the display 169 can comprise an LED screen. An audio signaling device 167 can also be provided to provide the user with information about the progress of the exercise, e.g., start, stop, type, speed, etc.

The control panel 160 is used to operate the device. The control panel 160 preferably has three control buttons: an on/off button 161, a select button 162, and an enter button 163. The on/off button 161 is used to manually turn the device 100 on or off. In one version of the device 100, if an exercise program is not started within a pre-determined time after the device is turned on, the device automatically shuts itself off. The select button 162 allows the user to choose an exercise program and is used to switch between the device functions. The device functions may include selection of the exercise program, setting the speed of the exercise, choosing an auditory feedback options, etc. The enter button 163 is used to operate the selected functions. The functions of the buttons may be altered in any manner known in the art.

The device 100 may store a variety of pre-set actions, operations or exercise programs. For example, the pre-set operations may include certain audio signals to indicate the end or the beginning of an exercise sequence, the display of an LED, a pause between exercises, display sequences for the LEDs 120 selectable by a user, and so on.

The device 100 may provide pre-determined preset speed settings. A speed setting can measure how long a single LED stays displayed or how fast the next LED is displayed. Depending on the speed setting, a given exercise sequence may be done different number of sequence cycles within a pre-determined exercise time (e.g., in the allotted one and one half minute, the Sequence Program I may be done one, two, three or more times depending on the speed setting). The table illustrates the device 100 that may have multiple speed settings, showing the display times for a single LED at each speed setting:

| Speed setting | Time of display for a single LED in a sequence (seconds) |
|---|---|
| 0 | 2.5 |
| 1 | 2.0 |
| 2 | 1.75 |
| 3 | 1.5 |
| 4 | 1.25 |
| 5 | 1.0 |

-continued

| Speed setting | Time of display for a single LED in a sequence (seconds) |
|---|---|
| 6 | .75 |
| 7 | .50 |
| 8 | .25 |
| 9 | .20 |
| C | Changeable speed setting: each LED stays on for a randomly changeable amount of time. |

The device 100 may be equipped with an auditory feedback option that provides auditory stimulus. The auditory feedback option serves to reinforce the eyes' ability to accurately locate the displayed light source(s). For this purpose, a sound can be generated every time an LED is about to be displayed or concurrently displayed. The sound goes on at the exact moment the LED turns on. Also, the device may beep to indicate the end of the exercise sequence, etc. The device may also produce a number of short beeps, for example, followed by one long beep, to indicate that an exercise program is about to begin, etc.

Some of the operations of the device 100 will now be described. Pressing the button 161 on the control panel 160 turns on the device. Once the device had been turned on, a "P" (for program) appears on the LED display 169. By pressing the select button 162 once, a number 1 (for program 1) is displayed on the display. Each time the button 162 is pressed, the display shows the program number associated with the next program. Once the program number of the last program is displayed, the device returns to the program 1.

After the desired program is selected, pressing the enter button 163 causes an "S" (for speed) to come up on the display. The select button 162 is used to set the speed of the device (e.g., the time each LED remains displayed in a sequential, one-at-a-time display of LED's). Initially, the display 169 shows a zero (0), indicating the slowest speed setting. Each successive time the select button 162 is pressed the speed setting advances to the next faster level (e.g., 2, 3, 4, etc.). Pressing the select button 162 again brings the speed setting back to zero (0).

In general, pressing the button 163 moves the user from program selection to speed selection to auditory feedback selection, etc. Thus, after the speed setting is selected, pressing the enter button 163 causes an "A" (for auditory feedback) to show up on the display 169. By pressing the select button 162 once, a "0" comes up on the display, indicating a "no" for auditory feedback. Pressing the select button 162 a second time causes a number "1" to come up on the display indicating a "yes" for auditory feedback. Pressing the select button one more time brings the auditory feedback setting back to zero ("0"). After selecting no (0) or yes (1) for auditory feedback, the enter button 163 is pressed. The device may now be used in eye exercises.

The above menu system is merely exemplary and other system of menus, icons, displays, etc. can be used for ease of user interaction.

The device 100 may be used for eye movement exercises, which may be performed horizontally, vertically, and in both oblique meridians. In each case, once the device 100 is programmed and oriented in the appropriate meridian, the observer stands or sits in front of the device and presses the enter button 163 to begin the exercise. The device runs the desired exercise program while the user's eyes track the movement of the displayed LEDs. Once proficiency is established, the observer may move closer or further away from the device 100, depending on the desired training effect. As the distance between the observer and the device shortens, the eye movement exercises begin to gently stretch the eye muscles. As the distance increases, the eyes begin developing greater fine-motor control.

The device 100 may also be used to exercise binocular vision while simultaneously providing the user feedback on whether the eyes are working together as a team or not. When a person with normally functioning eyes looks at a target, an area of single binocular vision is created. Points located within this area are seen singly. Points located in front of or behind this area of single binocular vision are perceived as double. This phenomenon is known as physiological diplopia. When a series of fixation targets (e.g., LEDs) are lined up in a straight line moving away from the eyes of the observer with normal binocular vision, the target specifically being viewed appears single while targets in front of and behind appear double. This use of physiological diplopia provides the user visible feedback about their eyes ability to work together as a team. Furthermore, if the fixation targets (e.g., the LED's 120) are connected by a stripe, a viewer with normal binocular vision will also see the appearance of an "X" with the target (LED) being fixated at its intersection. The appearance of an "X", along with the apparent doubling of the fixation targets (LED's) not being viewed, provides a visible feedback mechanism for the user about the degree to which their eyes work together as a team. This exercise specifically strengthens the user's ability to efficiently use both eyes together as a team during a dynamic situation because the user literally can see when both eyes are being used together and when they are not.

FIGS. 12A–12E illustrate examples of the eye exercises with the device of the invention.

EXAMPLE 1

Horizontal Eye Movement Exercises

Figure 12A:
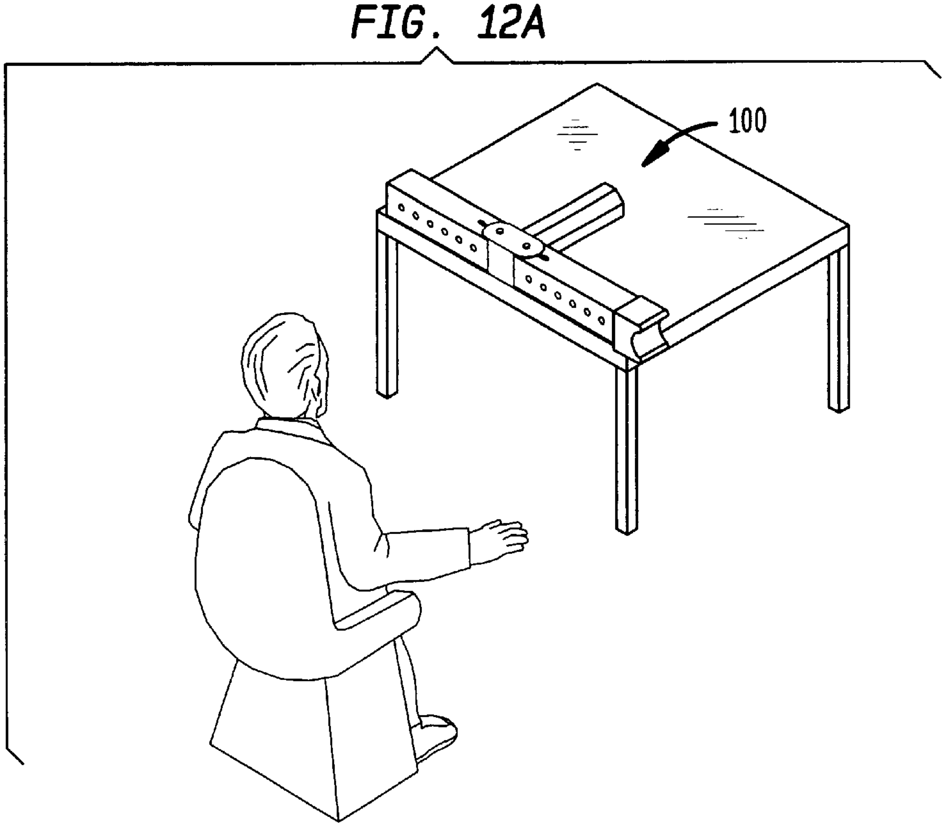
FIGS. 12A–12E illustrate examples of exercises with the eye exercise device of the preferred embodiment of the invention.

The device is set up at eye level, oriented for horizontal viewing (FIG. 12A). A chair is placed approximately one yard away from the device 100. The user presses the enter button 163 and sits down in the chair to begin the first eye movement exercise. Once the enter button 163 is pressed, the LED display 169 turns off and begins the auditory countdown to the exercise. For example, if the countdown is 10 seconds long, the device sounds a short beep every second for nine seconds followed by one long beep. The long beep informs the user that an exercise program is about to begin. Once the program begins, the LEDs 120 are displayed from left to right and back from right to left. The user is tracking the displayed LED with the eyes. The purpose of the exercise is to train the user to allow their eyes to move freely and accurately as they track a moving target. The program runs for one an one half minutes and then ends indicating the completion of the first exercise and the beginning of a break period. The user can now relax and gently breathe.

EXAMPLE 2

Vertical Eye Movement Exercises

Figure 12B:
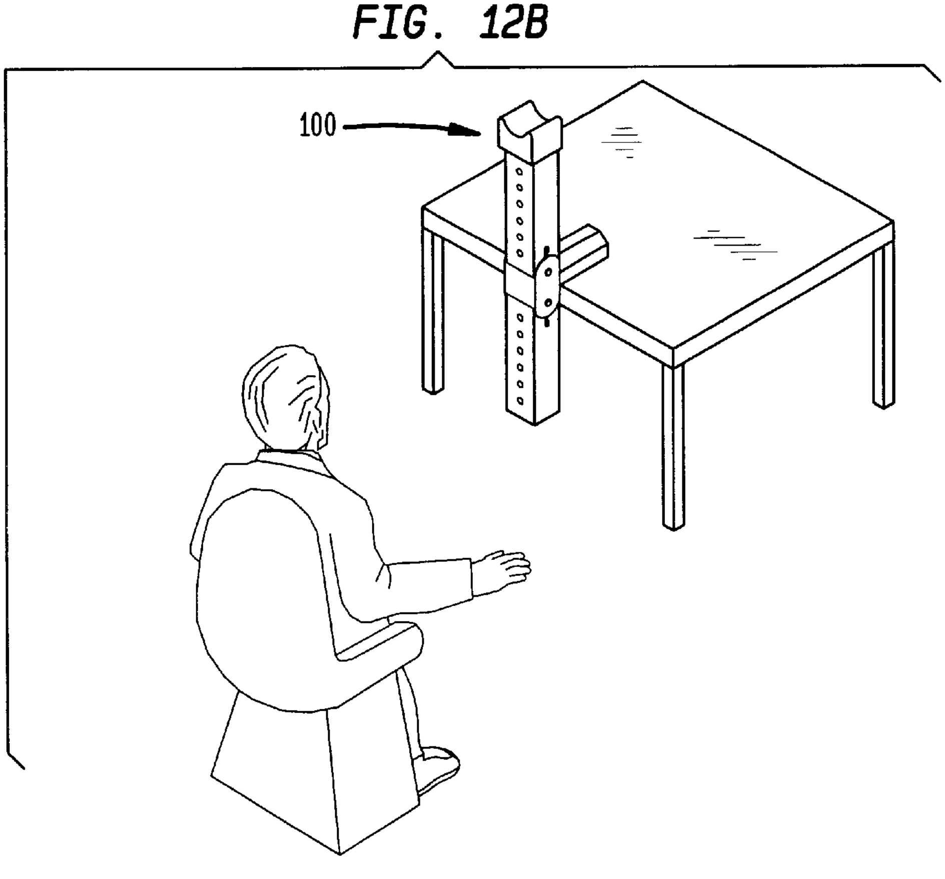

Once the break period ends, the device will beep twice for the next exercise. The device 100 is set up in a vertical orientation (FIG. 12B). The second exercise is the same as the first but is done in a vertical orientation. It trains vertical eye movements.

EXAMPLE 3

Oblique Eye Movement Exercises

Figure 12C:
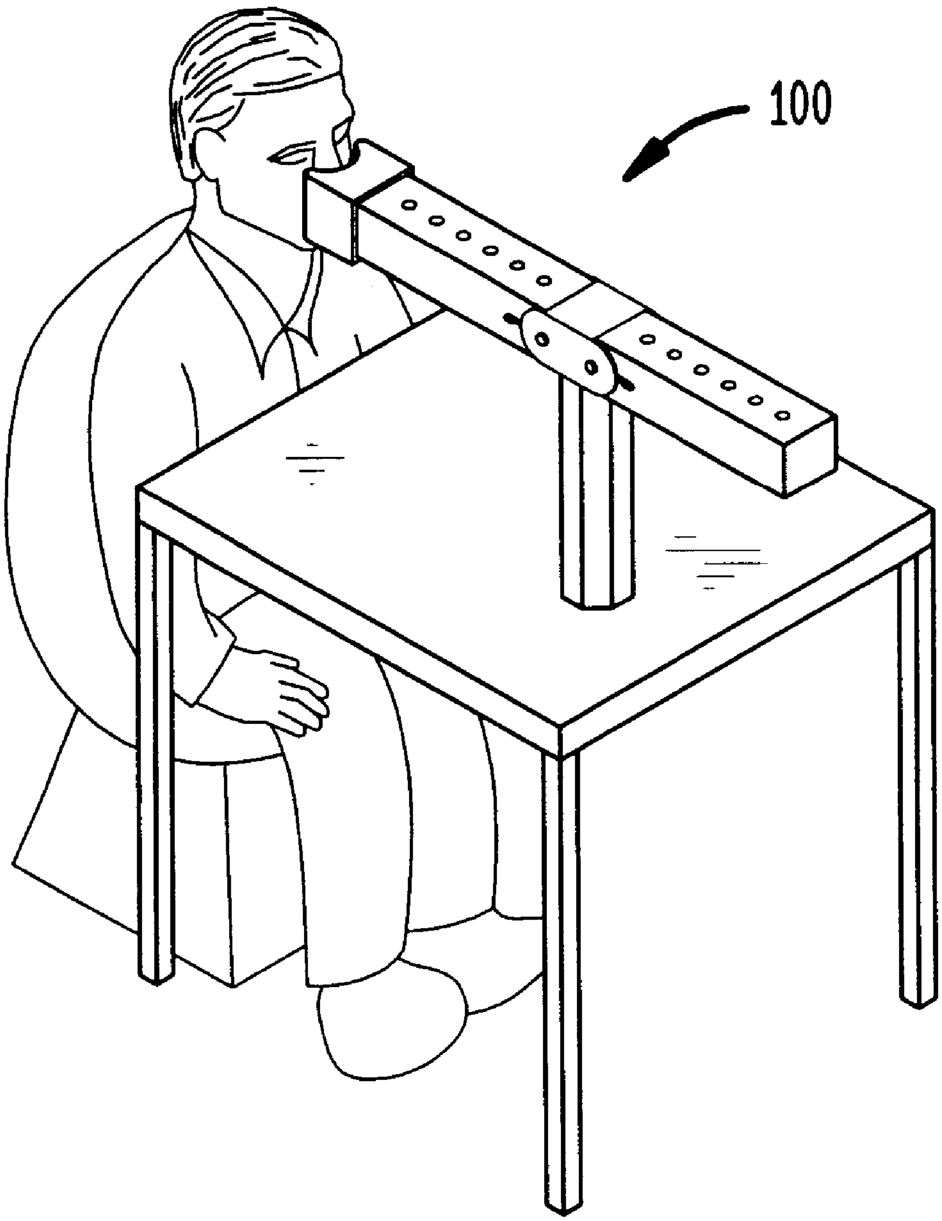
Figure 12D:
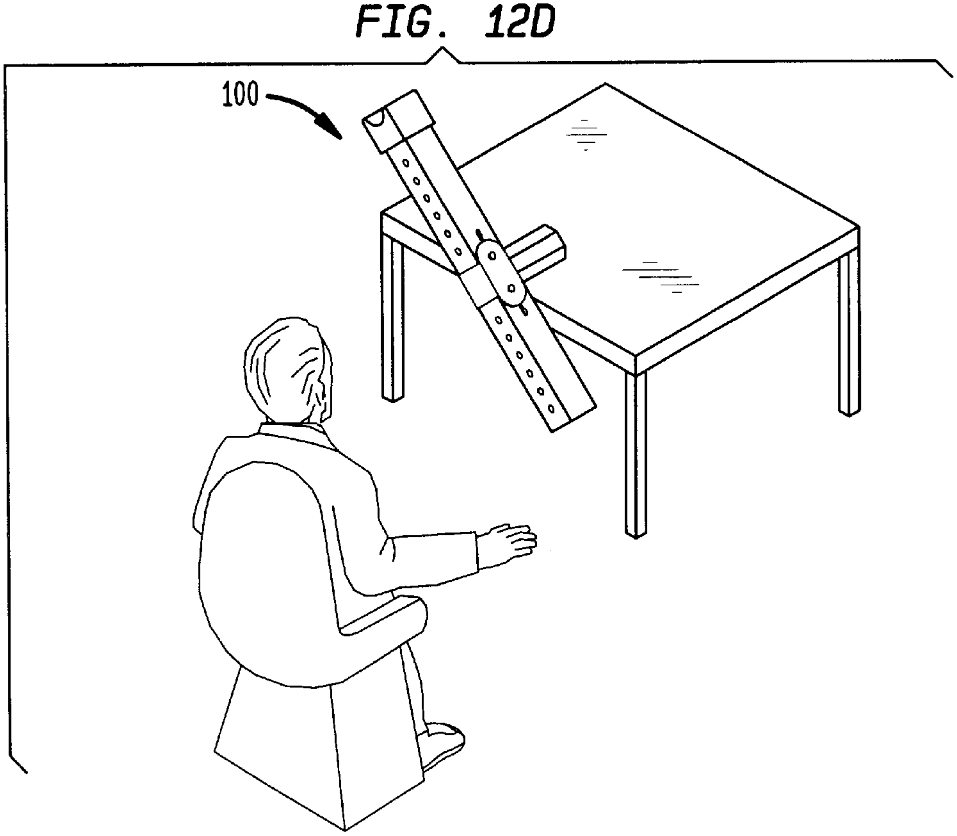
Figure 12E:
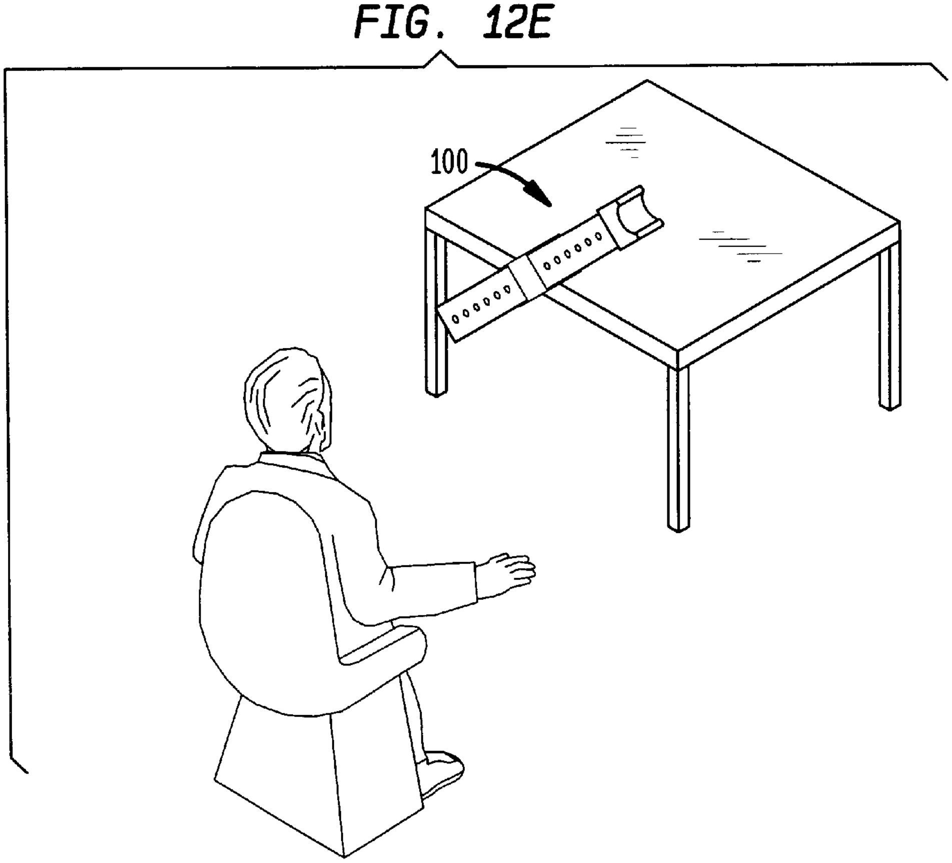

Other exercises are illustrated in FIGS. 12D and 12E. These exercises are the same as the first exercise, but are done in one of the oblique orientations. They train oblique eye movements.

EXAMPLE 4

Binocular Vision Exercises

The device 100 may also be used to train eye-teaming skills or binocular vision. An observer places the nose in the recessed bridge 139 at the end of the horizontal bar 130 (FIG. 12C). This insures appropriate nose placement. After one of the exercise programs is activated, one LED is displayed at a time, creating an impression of movement. The observer's eyes focus on each displayed LED, leaving the LED as it is turned off and focusing on the next turned on LED. This exercise trains the eyes to work efficiently as a team, expanding the range of binocular vision. The exercise also trains the ability to aim, focus and track more accurately and efficiently. The eyes naturally aim, track, focus and work together simultaneously. By exercising their ability to track a moving target all these functions are trained at the same time. By adding the alternating red and blue LED's the focusing and convergence mechanisms are gently rocked to one side and then the other of a desired center point, or point of perfect balance. The use of alternating red and blue LED's trains the visual system to continually "let go" of its point of fixation and move on to the next stimulus.

The preferred device of the invention may come with a special pair of eyeglasses with interchangeable red and blue (or violet) lenses. When these eyeglasses are used in combination with the red and blue LED's used in the device, a special cancellation effect occurs. The eye behind the red lens only sees the red LED, while the eye behind the blue lens only sees the blue LED. When these red/blue glasses are worn while tracking alternating red and blue LED's in an eye exercise program, a unique cancellation effect occurs. Each eye alternately exercises its individual ability to accurately and efficiently aim, focus and track a target, while simultaneously reinforcing its ability to work together as an equal partner with the other eye.

By using red/blue glasses in combination with alternating red and blue LED's, the user is able to alternately train each eye to become the lead eye, at any given moment. This exercise establishes a high degree of balance between the eyes by equalizing the contribution of each eye while the two eyes are working together. Additionally, by interchanging the lenses, you increase the effect experienced by each eye individually and further balance the ability of both eyes to work as a team. These special red/blue glasses can be used while doing any of the eye exercises recommended. When red/blue glasses are used in combination with alternating red and blue LED's, it results in the eyes alternately being switched on and off the fixation target. This process re-establishes the eye's natural fusional reflex so that the eyes once again begin seeing instinctively, accurately and effortlessly. Since the brain naturally receives signals from each eye in an alternating fashion, this exercise reinforces the natural coordination of the eyes and their inherent alternate information processing nature.

EXAMPLE 5

Exercise Sequences 1–3

The sequence programs 1–3 shown below are non-limiting examples of preset sequences. In each program, one LED is activated at a time. The order of display is shown from left to right, with LEDs 120 numbered from 1 to 12:

Sequence Program I.

LEDs 120 are displayed one at a time in the sequence 1→2→3→4→5→6→7→8→9→10→11→12→11→10→9→8→7→6→5→4→3→2→1→ . . . for 1½ minutes. Depending on the selected speed, the cycle repeats one, two or more times during the 1½ minute exercise sequence.

Sequence Program II.

The LED's 120 are displayed one at a time in the sequence 1→12→2→11→3→10→4→9→5→8→6→7→5→8→4→9→3→10→2→11→1→12→ . . . for 1½ minutes. Depending on the selected speed, the cycle repeats one, two or more times during the 1½ minute exercise sequence.

Sequence Program III. The LED's 120 are displayed randomly for 1½ minutes.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An eye exercise device comprising:

a) a housing, including a plurality of colored light sources arranged to be viewable by at least one eye of an observer and disposed in a substantially linear alignment, said colored light sources including
   - a first and third color which causes the eye to increase its focusing power to gain a sharp image of said first color, and
   - a second and fourth color which causes the eye to decrease its focusing power to gain a sharp image of said second color, said second color being different than said first color, said third color being different than said second color and said fourth color being different than said third color; and b) a controller for sequentially controlling the display of each of said light sources to at least one eye of an observer, the linear arrangement comprising, sequentially, one or more colored light sources of said first color, one or more light sources of said second color, one or more light sources of a third color, and one or more light sources of a fourth color.

2. The device of claim 1, wherein the first and third colors are the same and the second and fourth colors are the same.

3. The device of claim 2, wherein said first and third colors are red, and said second and fourth colors are blue or violet.

4. The device of claim 3, wherein said housing includes a horizontal bar having two ends; said device further comprising a handle connected to said horizontal bar between said two ends.

5. The device of claim 4, wherein said horizontal bar includes a top surface and a bottom surface, said plurality of light sources are mounted on said top surface of said horizontal bar, and said handle extends from said bottom surface of said horizontal bar.

6. The device of claim 5, wherein said horizontal bar comprises foldable segment portions thereby providing an operational position wherein said horizontal bar is substantially perpendicular to said handle and a storage position wherein said horizontal bar is folded.

7. The device of claim 6, wherein at least one of said two ends of said horizontal bar comprises a recess for stabilizing the position of an observer.

8. The device of claim 6, wherein said light sources are substantially equidistant from each other.

9. The device of claim 6, wherein said top surface of said horizontal bar includes a linear marking element extending substantially between said two ends of said horizontal bar.

10. The device of claim 1, wherein said first and third colors are selected from the group consisting of orange and red, and said second and fourth colors are selected from the group consisting of violet, indigo, turquoise, and blue.

11. The device of claim 1, wherein said light sources are light emitting diodes.

12. The device of claim 1, further comprising a control panel for user adjustment of said controller.

13. An eye exercise device comprising:

a) two or more first light sources of a first color which causes eye to increase its focusing power to gain a sharp image of said first light sources, b) two or more second light sources of a second color different from said first color which causes each eye to decrease its focusing power to gain a sharp image of said second light sources;

c) a housing to which said first and second light sources are mounted; and d) a controller operative to alternate the display of said first and second light sources in a pre-determined pattern to repeatedly present to at least one eye only one of said first light sources and then only one of said second light sources to exercise the at least one eye by alternately causing an increase and decrease in the focusing power of the at least one eye viewing said light sources.

14. The device of claim 13, wherein said first color is selected from the group consisting of orange and red, and said second color is selected from the group consisting of violet, indigo, turquoise, and blue.

15. The device of claim 13, wherein said first color is red, and said second color is blue or violet.

16. The device of claim 15, wherein said device comprises a plurality of said red light sources and a plurality of said blue or violet light sources.

17. An eye exercise device comprising:

a) a plurality of red light sources which causes the eye to increase the focusing power of the eye to gain a sharp image of said red light sources, b) a plurality of blue or violet light sources which causes the eye to decrease the focusing power of the eye to gain a sharp image of said blue or violet light sources;

c) a housing to which said red and blue or violet light sources are mounted in an alternating arrangement to each other; and d) a controller operative to alternate the display of said red and blue or violet light sources in a pre-determined pattern to exercise one or more eyes of the observer's eye by alternately causing an increase and decrease in the focusing power of an eye of an observer viewing said light sources.

18. The device of claim 17, further comprising a handle and a base connected to said handle, said housing including a foldable horizontal bar having two ends, a top surface and a bottom surface, said blue and red light sources mounted on said top surface and, said handle extending from said bottom surface, said foldable horizontal bar being connected to said handle at a location that divides said horizontal bar into two segments, each segment extending from one of said two ends of said horizontal bar to said connection location;

said device having an operational position in which said horizontal bar is substantially perpendicular to said handle and said blue and red light sources are in a substantially linear alignment, and a storage position wherein said horizontal bar is folded thereby said two segments of said horizontal bar are substantially parallel with and laying adjacent to said handle.

19. The device of claim 18, wherein said handle has octagonal or square shape.

20. A method of exercising an eye of an observer comprising:

a. exposing at least one eye of the observer to a predetermined arrangement of (i) one or more first light sources of a first color that causes the eye to increase the focusing power to gain a sharp image of said first light sources, and (ii) one or more second light sources of a second color different than said first color that causes the eye to decrease the focusing power to gain a sharp image of said second light sources; and b. alternating the display of said first and second light sources the at least one eye to exercise the at least one eye of the observer observing said light sources by alternately causing said focusing power to increase and decrease.

21. The method of claim 20, wherein the alternating comprises alternating the display between said first color being selected from the group consisting of orange and red, and said second color being selected from the group consisting of violet, indigo, turquoise, and blue.

22. The method of claim 20, wherein said first color is red, and said second color is blue or violet.

23. The method of claim 20, wherein said pre-determined arrangement is a substantially linear alignment of said light sources.

24. The method of claim 23, further comprising positioning said observer vertically in front of said substantially linear alignment of said light sources.

25. The method of claim 24, further comprising positioning said light sources and the eyes of the observer at an approximately the same level.

26. The method of claim 25, further comprising placing said light sources so that a vertical plane containing said substantially linear alignment of said light sources and a vertical plane containing an imaginary line drawn through the eyes of the observer are substantially parallel to each other.

27. The method of claim 26, further comprising placing said substantially linear alignment of said light sources in a horizontal, oblique, or vertical position with respect to a horizontal plane containing the eyes of the observer.

28. The method of claim 27, further comprising exposing the observer to a discreet exercise sequence, changing a distance between the observer and said light sources, and exposing the observer to another discreet exercise sequence.

29. The method of claim 26, further comprising consecutively activating one of said light source at a time.

30. The method of claim 25, further comprising placing said light sources so that a vertical plane containing said substantially linear alignment of said light sources and a vertical plane containing an imaginary line drawn through the eyes of the observer are substantially perpendicular to each other.

31. The method of claim 30, further comprising consecutively activating one of said light source at a time.

32. The method of claim 20, further comprising simultaneously exercising both eyes of the observer.

33. A method of exercising one or both eyes of an observer, comprising (a) exposing one or both eyes of the observer to a plurality of red and blue light sources, (b) activating one or more of said light sources to display said light sources to the one or both eyes of the observer one-at-a-time, and providing said red light sources and said blue light sources mounted in an alternating arrangement with each other.

* * * * *

UNITED STATES PATENT AND TRADEMARK OFFICE

CERTIFICATE OF CORRECTION

PATENT NO. : 6,742,892 B2
DATED : June 1, 2004
INVENTOR(S) : Jacob Liberman

It is certified that error appears in the above-identified patent and that said Letters Patent is hereby corrected as shown below:

Title page,
Item [57], ABSTRACT, line 1, "is" should read -- are --.

Column 1,
Line 19, "have" should read -- has --.

Column 3,
Line 39, "Suppose," should read -- Suppose --.

Column 9,
Line 3, after "of" insert -- the --.

Column 12,
Line 5, "a" should read -- an --.

Column 13,
Line 49, after "done" insert -- a --.

Column 18,
Line 26, after "causes" insert -- each --.

Column 19,
Line 18, before "octagonal" insert -- an --.
Line 30, after "sources" insert -- to --.

UNITED STATES PATENT AND TRADEMARK OFFICE

CERTIFICATE OF CORRECTION

PATENT NO. : 6,742,892 B2
DATED : June 1, 2004
INVENTOR(S) : Jacob Liberman

It is certified that error appears in the above-identified patent and that said Letters Patent is hereby corrected as shown below:

Column 20,
Line 5, delete the word "an".
Lines 23 and 31, "source"should read -- sources --.

Signed and Sealed this

Thirty-first Day of August, 2004

JON W. DUDAS
*Director of the United States Patent and Trademark Office*

UNITED STATES PATENT AND TRADEMARK OFFICE

CERTIFICATE OF CORRECTION

PATENT NO. : 6,742,892 B2
APPLICATION NO. : 10/123594
DATED : June 1, 2004
INVENTOR(S) : Jacob Liberman It is certified that error appears in the above-identified patent and that said Letters Patent is hereby corrected as shown below:

Title page,
Item [57], ABSTRACT, line 1, “is” should read -- are --.

Column 1,
Line 19, “have” should read -- has --.

Column 3,
Line 39, “Suppose,” should read -- Suppose --.

Column 9,
Line 3, after “of” insert -- the --.

Column 12,
Line 5, “a” should read -- an --.

Column 13,
Line 49, after “done” insert -- a --.

Column 15,
Line 55, “their” should read -- his or her --.

Column 18,
Line 26, after “causes” insert -- each --.

Column 19,
Line 18, before “octagonal” insert -- an --.
Line 30, after “sources” insert -- to --.

UNITED STATES PATENT AND TRADEMARK OFFICE

CERTIFICATE OF CORRECTION

PATENT NO. : 6,742,892 B2
APPLICATION NO. : 10/123594
DATED : June 1, 2004
INVENTOR(S) : Jacob Liberman It is certified that error appears in the above-identified patent and that said Letters Patent is hereby corrected as shown below:

<u>Column 20</u>,
Line 5, delete the word “an”.
Lines 23 and 31, “source”should read -- sources --.

This certificate supersedes Certificate of Correction issued August 31, 2004.

Signed and Sealed this

Twenty-first Day of November, 2006

JON W. DUDAS
*Director of the United States Patent and Trademark Office*